(12) United States Patent
Cui et al.

(10) Patent No.: US 11,291,667 B2
(45) Date of Patent: Apr. 5, 2022

(54) COMBINATION THERAPY INVOLVING DIARYL MACROCYCLIC COMPOUNDS

(71) Applicant: TURNING POINT THERAPEUTICS, INC., San Diego, CA (US)

(72) Inventors: Jingrong Jean Cui, San Diego, CA (US); Dayong Zhai, San Diego, CA (US)

(73) Assignee: TURNING POINT THERAPEUTICS, INC., San Diego, CA (US)

( * ) Notice: Subject to any disclaimer, the term of this patent is extended or adjusted under 35 U.S.C. 154(b) by 176 days.

(21) Appl. No.: 16/480,557

(22) PCT Filed: Jan. 25, 2018

(86) PCT No.: PCT/US2018/015150
§ 371 (c)(1),
(2) Date: Jul. 24, 2019

(87) PCT Pub. No.: WO2018/140554
PCT Pub. Date: Aug. 2, 2018

(65) Prior Publication Data
US 2019/0381048 A1    Dec. 19, 2019

Related U.S. Application Data

(60) Provisional application No. 62/619,165, filed on Jan. 19, 2018, provisional application No. 62/450,455, filed on Jan. 25, 2017.

(51) Int. Cl.

| | | |
|---|---|---|
| A61K 31/519 | (2006.01) | |
| A61P 35/00 | (2006.01) | |
| A61K 31/506 | (2006.01) | |
| A61K 31/517 | (2006.01) | |
| A61K 31/5377 | (2006.01) | |
| A61K 39/395 | (2006.01) | |

(52) U.S. Cl.
CPC .......... *A61K 31/519* (2013.01); *A61K 31/506* (2013.01); *A61K 31/517* (2013.01); *A61K 31/5377* (2013.01); *A61K 39/3955* (2013.01); *A61P 35/00* (2018.01)

(58) Field of Classification Search
CPC .. A61K 31/519; A61K 31/506; A61K 31/517; A61K 31/5377; A61K 39/3955; A61K 45/06; A61P 35/00; C07D 498/18
See application file for complete search history.

(56) References Cited

U.S. PATENT DOCUMENTS

| | | | |
|---|---|---|---|
| 5,639,778 | A | 6/1997 | Andersson |
| 5,698,578 | A | 12/1997 | Heath, Jr. |
| 8,497,270 | B2 | 7/2013 | Thuring |
| 8,680,111 | B2 | 3/2014 | Bailey |
| 8,815,872 | B2 | 8/2014 | Yu |
| 8,933,084 | B2 | 1/2015 | Andrews |
| 9,714,258 | B2 | 7/2017 | Cui |
| 10,246,466 | B2 | 4/2019 | Cui |
| 10,294,242 | B2 | 5/2019 | Cui |
| 10,316,044 | B2 | 6/2019 | Cui |
| 2011/0294801 | A1 | 12/2011 | Yu |
| 2013/0034495 | A1 | 2/2013 | Beauchamps et al. |
| 2013/0143895 | A1 | 6/2013 | McAllister et al. |
| 2013/0203776 | A1 | 8/2013 | Andrews |
| 2013/0245021 | A1 | 9/2013 | Bi |
| 2013/0252961 | A1 | 9/2013 | Bailey |
| 2014/0107099 | A1 | 4/2014 | Blaney |
| 2014/0206605 | A1 | 7/2014 | Beutner |
| 2016/0339027 | A1 | 11/2016 | Carter |
| 2017/0002023 | A1 | 1/2017 | Cui et al. |
| 2017/0240545 | A1* | 8/2017 | He .......................... A61P 35/00 |
| 2017/0334929 | A1 | 11/2017 | Cui |
| 2018/0186813 | A1 | 7/2018 | Cui |
| 2018/0194777 | A1 | 7/2018 | Cui |
| 2018/0325901 | A1 | 11/2018 | Cui |

FOREIGN PATENT DOCUMENTS

| | | |
|---|---|---|
| CL | 2012003227 | 2/2013 |
| CN | 102143750 | 8/2011 |
| CN | 102971322 | 3/2013 |
| EA | 003640 B1 | 8/2003 |
| EP | 3573991 A | 12/2019 |
| JP | 2012502043 | 1/2012 |
| WO | 2002046197 A | 6/2002 |
| WO | 2010028116 | 3/2010 |
| WO | 2010033941 | 3/2010 |
| WO | 2010048314 | 4/2010 |
| WO | 2010051549 | 5/2010 |
| WO | 2011146336 | 11/2011 |

(Continued)

OTHER PUBLICATIONS

Janne, et al. N Engl J Med Apr. 30, 2015;372(18):1689-99 (Year: 2015).*
De Pas, et al., Journal of Clinical Oncology 2011 vol. 29 No. 34, pp. 819-822 (Year: 2011).*
Okamoto, et al., Annals of Oncology, 2006 vol. 17 No. 6, pp. 1028-1029 (Year: 2006).*
Karachaliou, et al., EBioMedicine 2018 29, 122-127 (Year: 2018).*
Pierotti, M.A. et al., Cancer Lett. 2006, 232, 90-98.
Vaishnavi, A. et al., Nat. Med. 2013, 19, 1469-1472.
Verma, A. etal., Mol. CancerTher. 2011, JO, 1763-1773.
Zhang, Z. et al., Nat. Genet. 2012, 44, 852-860.
Cui, J. J. et al., J. Med. Chem. 2011, 54, 6342-6363.
Katayama, R. et al., Sci. Transl. Med. 2012, 4, 120ra17.
Quintas-Cardama, A. et al., Nat. Rev. Drug Discov. 2011, 10(2), 127-40.

(Continued)

*Primary Examiner* — Julie Wu
*Assistant Examiner* — John L Van Druff
(74) *Attorney, Agent, or Firm* — Mintz, Levin, Cohn, Ferris, Glovsky and Popeo, P.C.

(57) ABSTRACT

The present disclosure relates to methods and compositions for treating cancer with a diaryl macrocycle in combination with at least one other cancer therapeutic, such as an EGFR inhibitor.

15 Claims, 11 Drawing Sheets

(56) References Cited

FOREIGN PATENT DOCUMENTS

| WO | 2012034091 | | 3/2012 | |
|---|---|---|---|---|
| WO | 2012136859 | | 10/2012 | |
| WO | 2013001310 | | 1/2013 | |
| WO | 2013028465 | | 2/2013 | |
| WO | 2013045653 | | 4/2013 | |
| WO | 2013132376 | | 9/2013 | |
| WO | 2013134219 | | 9/2013 | |
| WO | 2013134228 | | 9/2013 | |
| WO | 2013147711 | | 10/2013 | |
| WO | 2015112806 | | 7/2015 | |
| WO | WO-2015112806 | A2 * | 7/2015 | ............ A61P 37/08 |
| WO | 2017004342 | | 1/2017 | |
| WO | 2017007759 | | 1/2017 | |
| WO | 2017015367 | | 1/2017 | |
| WO | 2018022911 | | 2/2018 | |
| WO | 2018140554 | | 8/2018 | |
| WO | 2019023417 | | 1/2019 | |
| WO | 2019120267 | | 6/2019 | |
| WO | 2019201282 | | 10/2019 | |

OTHER PUBLICATIONS

Pesu, M. et al., Immunol. Rev. 2008, 223, 132-142.
Murray, P.J., J. Immunol. 2007, 178(5), 2623-2329.
Muller, M. et al., Nature 1993, 366(6451), 129-135.
Neubauer, H. et al., Cell 1998 93(3), 397-409.
Nosaka, T. et al., Science 1995, 270(5237), 800-802.
Vainchenker, W. et al., Semin. Cell. Dev. Biol. 2008, 19(4), 385-393.
Levine, R.L. et al., Cancer Cell 2005, 7(4), 387-397.
Kralovics, R. et al., N. Engl. J. Med. 2005, 253(17), 1779-1790.
James, C. et al., Nature 2005, 434(7037), 1144-1148.
Baxter, E.J. et al. Lancet 2005, 365(9464), 1054-1061.
Sonbol, M.B. et al., Ther. Adv. Hematol. 2013, 4(1), 15-35.
LaFave, L.M. et al., Trends Pharmacol. Sci. 2012, 33(11), 574-582.
Verstovsek, S. et al., N. Engl. J. Med. 2012, 366(9), 799-807.
Quintas-Cardama, A. et al., Blood 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al., Genes Chromosomes Cancer 2003, 37, 58.
Takeuchi K, et al. Nat. Med. 2012, 18, 378.
Gu TL, et al. PLoS One. 2011, 6, e15640.
Lacronique V, et al. Science 1997, 278, 5341, 1309-12.
Reiter A, et al. Cancer Res. 2005, 65, 7, 2662-7.
Zhang S, et al. Trends Pharmacol Sci. 2012, 33, 122.
Bromann PA, Oncogene 2004, 23, 7957-7968.
Summy JM, et al. Cancer Metastasis Rev. 2003, 22, 337-358.
Scancier F. et al. PLoS One. 2011, 6(2): e1 7237.
Ongusaha PP, et al. EMBO J. 2003, 22, 1289-1301.
Hammerman PS, et al. Cancer Discov. 2011, 1, 78-89.
Tomasson MH, et al. Blood 2008, 111:4797-4808.
Yu J. et al., Cancer Cell, 2010, 17, 5, 443-54.
Advani, A.S. et al. Leukemia Research, 2002, 26, 8, 713-720.
Gottesman, M.M., Annu. Rev. Med., 2002, 53, 615-627.
Anastassiadis T, et al Nat Biotechnol. 2011, 29, 1039.
Vetrie D. et al. Nature 1993, 361, 226-233.
Mohamed AJ et al, immunological Reviews, 2009, 228, 58-73.
Grande, E. et al., Mol. Cancer Ther. 2011, 10, 569-579.
Monti, E. 2007. Molecular Determinants of Intrinsic Multidrug Resistance in Cancer Cells and Tumors In B. Teicher (Ed.), Cancer Drug Resistance (pp. 241-260).
McCarthy et al. "Tropomyosin receptor kinase inhibitors: a patent update 2009-2013," Expert Opinions 2014, pp. 731-744.
Sen, B., et al. Distinct interactions between SRC and MET in mediating resistance to SRC inhibition in head and neck cancer. Clin Cancer Res. 2010, 17, 1-11.
Yu, Helena A., et al. Analysis of tumor specimens at the time of acquired resistance to EGFR-TKI therapy in 155 patients with EGFR-mutant lung cancers. Clin. Cancer Res. 2013, 19, 2240-2247.
Xie, Q., et al. Hepatocyte growth factor (HGF) autocrine activation predicts sensitivity to MET inhibition in alioblastoma. Proc. Natl. Acad. Sci. U.S. A. 2012, 109, 570-575.
PubChem-CID98009788,Create Date: Dec. 11, 2015 (Dec. 11, 2015).
Peterson et al., "Expanding the Scope of Crystal Form Evaluation in Parmaceutical Science" Journal of Pharmacy & Pharmaceutical Science 2006 9(3):317-326.
Lin et al., "Targeting ALK: Precision Medicine Takes on Drug Resistance", Cancer Discov., Feb. 2017; 7(2): 137-155. Published online Jan. 25, 2017.
Pennacchietti et al., "Microenvironment-Derived HGF Overcomes Genetically Determined Sensitivity Anti-MET Drugs", Cancer Res. Nov. 15, 2014; 74(22): 6598-609. Published online Sep. 12, 2014.
Lim et al., "Discovery of 5-Amino-N-(1H-pyrazol-4-yl)pyrazolo[1,5-a]pyrimidine-3-carboxamide Inhibitors of IRAK4," ACS Medicinal Chemistry Letters (2015), 6(6), 683-688.
Zou et al., "PF-06463922 is a potent and selective next-generation ROS1/ALK inhibitor capable of blocking crizotinib-resistant ROS1 mutations", PNAS, Mar. 17, 2015, vol. 112, No. 11, 3493-3498.
Johnson et al., "Discovery of (10R)-7-Amino-12-fluoro-2,10,16-trimethyl-15-oxo-10,15,16,17-tetrahydro-2H-8,4-(methano)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations", J. Med. Chem., Jun. 12, 2014, 57, 4720-4744.
Jordan, "Tamoxifen: A Most Unlikely Pioneering Medicine", Nature Reviews, vol. 2, Mar. 2003, pp. 205-213.
Hackam et al., "Translation of Research evidence From Animals to Humans", JAMA, 2006; 296(14): 1731-1732.
Gargalionis et al., "The molecular rationale of Src inhibition in colorectal carcinomas", Int. J. Cancer: 134, 2019-2029 (2014). Published online Jun. 21, 2013.
Okamoto et al., "Identification of c-Src as a Potential Activation as a Cause of Resistance to c-Src Published online Apr. 20, 2010 Inhibition", Therapeutic Target for Gastric Cancer and of MET Mol Cancer Ther., May 2010; 9(5): 1188-97.
Vergani et al., "Identification of MET and SRC Activation in Melanoma Cell Lines Showing Primary Resistance to PLX4032", Neoplasia. Dec. 2011; 13(12): 1132-42.
Pachter et al., "The Chemistry of Hortiamine and 6-Methoxyrhetsinine," J. Am. Chem. Soc., 1961, 83, 635-642.
Kiselyov, Alexander S., "Solid support synthesis of 15-membered macrocycles containing a serotonin unit," Tetrahedron Letters 46 (2005) 3007-3010.
Halland et al. "Small Macrocycles As Highly Active Integrin 0131 Antagonists," ACS Medicinal Chemistry Letters, Jan. 10, 2014, 5, 193-198.
International Search Report and Written Opinion prepared for PCT/US2017/044214, dated Dec. 1, 2017, 11 pages.
Couronne L, et al. Blood 2013, 122, 811.
Di Paolo JA, et al. Nature Chemical Bioloav 2011, 7, 41-50.
Schiller J H et al., N Engl J Med, 346: 92-98, 2002.
Takahashi, M. et al. Cell. 1985, 42:581-588.
Pachnis, V., et al. Development 1993, 119, 1005-1017.
Schuchardt, A. et al. Nature 1994, 367:380-383.
Grieco, M. et al. Cell. 1990, 23; 60 (4):557-63.
Gainor JF, Shaw AT. Oncologist. 2013, 18(7):865-75.
Kentsis, A., et al. Autocrine activation of the MET receptor tyrosine kinase in acute myeloid leukemia. Nat. Medd. 2012, 18, 1118-1122.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the Mli'T Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.

(56) References Cited

OTHER PUBLICATIONS

Harbinski, F., et al. Rescue screens with secreted proteins reveal compensatory potential of receptor tyrosine kinases in driving cancer growth. Cancer Discov. 2012, 2, 948-959.
Parsons, S. J., et al. Src family kinases, key regulators of signal transduction. Oncogene, 2004, 23, 7906-7909.
Wojcik, E. J., et al. A novel activating function of SRC and STAT3 on HGF transcription in mammary carcinoma cells. Oncogene. 2006, 25, 2773-84.
Dulak AM et al. HGF-independent potentiation of EGFR action by Mli'l'. Oncogene. 2011, 30, 3625-3635.
Stabile, L. P., et al. c-SRC activation mediates erlotinib resistance in head and neck cancer by stimulating MET. Clin Cancer Res. 2012, 19, 1-13.
Bertotti, A., et al. Inhibition of SRC impairs the growth of MET-addicted gastric tumors. Clin Cancer Res. 2010, 16, 3933-3943.
Wrobel CN, et al. Autocrine CSFIR activation promotes SRC-dependent disruption of mammary epithelial architecture. J Cell Biol. 2004, 165, 263-273.
Ravi V, et al. Treatment of tenosynovial giant cell tumor and pigmented villonodular synovitis. Curr Opin Oncol. 2011, 23, 361-366.
Gridelli, C. et al., Cancer Treat Rev. 2014, 40, 300-306.
Liu Z, et al. J. Clin. Endocrinol. Metab. 2004, 89, 3503-3509.
Cooper, C. S., et al. Molecular cloning of a new transforming gene from a chemically transformed human cell line. Nature 1984, 311, 29-33.
Boccaccio, C.; Comoglio, P. M. Invasive growth: a MET-driven generic programme for cancer and stem cells. Nat. Rev. Cancer 2006, 6, 637-645.
Ma, PC et al. Expression and mutational analysis of MET in human solid cancers. Genes Chromosomes Cancer 2008, 47, 1025-1037.
Maulik, G., et al. Role of the hepatocyte growth factor receptor, MET, in oncogenesis and potential for therapeutic inhibition. Cytokine Growth Factor Rev. 2002, 13, 41-59.
Smolen, G. A., et al. Amplification of MET may identify a subset of cancers with extreme sensitivity to the selective tyrosine kinase inhibitor PHA-665752. Proc. Natl. Acad. Sci. U.S. A. 2006, 103, 2316-2321.
Ghiso, E.; Giordano, S. Targeting MET: why, where and how? Curr. Opin. Pharmacol. 2013, 13, 511-518.
Otsuka, T., et al. MET autocrine activation induces development of malignant melanoma and acquisition of the metastatic phenotype. Cancer Res. 1998, 58, 5157-5167.
Sawyers, C., Nature 2004, 432, 294-297.
Park, M. et al., Cell 1986, 45, 895-904.
Bottaro, D. P. etal., Science 1991, 251, 802-804.
Trusolino, L. et al., Nature Rev. Mol. Cell Biol. 2010, 11, 834-848.
Gherardi, E. et al., Nature Rev. Cancer 2012, 12, 89-103.
Engelman, J. A. et al., Science 2007, 316, 1039-1043.
Wilson, T.R. et al., Nature 2012, 487, 505-509.
Pulford, K. et al., Cell Mol. Life Sci. 2004, 61, 2939.
Manning, G. et al., Science 2002, 298, 1912-1934.
Morris, S.W. et al., Science 1994, 263, 1281.
Bischof, D. et al., Mol. Cell Biol., 1997, 17, 2312-2325.
Soda, M. et al., Nature 2007, 448, 561-566.
Mosse, Y. P. et al., Nature 2008, 455, 930-935.
Thiele, C. J. et al., Clin. Cancer Res. 2009, 15, 5962-5967.
International Preliminary Report on Patentability received for PCT Application No. PCT/US2018/015150, dated Aug. 8, 2019, 6 pages.
Belikov, V.G. (2007) "Farmatsevticheskaya Khimiya (Pharmaceutical Chemistry: A Manual)", Moscow: MEDpress-Inform, 27-29, 10 pages.
Tan et al. (Jan. 8, 2016) "Next-Generation Epidermal Growth Factor Receptor Tryrosine Kinase Inhibitors In Epidermal Growth Factor Receptor-Mutant Non-Small Cell Lung Cancer", Lung Cancer, 93:59-68, 10 pages.
Miller et al., "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.
International Search Report and Written Opinion prepared for PCT/US2015/012597, dated Aug. 28, 2015, 11 pages.
International Search Report and Written Opinion prepared for PCT/US2016/040329, dated Sep. 7, 2016, 13 pages.
International Search Report and Written Opinion prepared for PCT/US2016/040972, dated Sep. 13, 2016, 8 pages.
European Search Report issued in EP 16828471, completed Mar. 15, 2019.
European Search Report issued in EP 16818768, completed Jan. 22, 2019.
Wiesner T, et al. Nature 2015, 526, 453-457.
Voena C, et al. Oncotarget, Apr. 23, 2016, 8955.
Uguen A, et al. Future Oncol. Jun. 3, 2016, Epub ahead of print.
Gao SP, et al. Sci Signal. 206, 9 (421):ra33: published online Mar. 29, 2016.
Balko JM, et al. Sci Transl Med. 2016, 8 (334):ra53, published Apr. 13, 2016.
Liu W, et al. Oncotarget 2015, 6: 35522-35541.
Serrels A, et al. Cells 2015, 163, 160-173.
Shi L, et al. Br J Cancer. 2014, 111(12): 2316-27.
Xu T, et al. Cancer Lett. 2016, 377(2): 140-8, published online Apr. 25, 2016.
Elias D., et al. Pharmacological Research 2015, 100, 250-254.
Ambrogio C, et al., Nature Medicine, 2016, 22, 270-277, published Feb. 8, 2016.
Bender AT, et al. Clinical Immunology 2016, 164, 65-77, available online Jan. 25, 2016.
Morgillo F, Della Corte CM, Fasano M. et al. Mechanisms of resistance to EGFR-targeted drugs: lunch cancer. ESMO Open 2016;1: e000060, published online May 11, 2016.
Pubchem, Compound Summary for SID 252159180, available date; Aug. 10, 2015, retrieved Aug. 31, 2017, retrieved from: https://pubchem.ncbi.nlm.nih.gov/substance/252159180.
Rahal, "The development of Potent and Selective RET inhibitors", Presentation at Annual AACR Meeting, Apr. 18, 2016.
Jiang H, et al. Nat Med. Jul. 4, 2016, [Epub ahead of print].
Toso, A. et al., Cell Reports 2014, 9, 75-89.
Shaw, A. T. et al., N Engl J Med. 2014, 371(21):1963-1971.
International Search Report and Written Opinion prepared for PCT/US2016/043132, dated Sep. 28, 2016, 8 pages.
Politi K, Clin Cancer Res. 2014, 20, 5576.
Crystal AS, Science. 2014, 346, 1480.
Vaishnavi A, et al. Cancer Discov. 2015, 5, 25.
Park, K-S, et al. J Clin Invest. 2014, 124(7):3003-3015.
Golubovskaya VM, Front Biosci (Landmark Ed). ; 19: 687-706.
Liu L, et al. Nature, 2012, 483, 608-612.
Stransky N, et al. Nature Communications 2014, 5, 4846.
Schwarz LJ, et al. J Clin Invest. 2014, 124, 5490-5502.
Zardan A., et al. Oncogenesis 2014, 3, e 115.
Rudd ML, etal. BMC Cancer 2014, 14, 884.
Furman RR, et al. New England Journal of Medicine, 2014, 370, 2352-2354.
Buchert M, et al. Oncogene, 2016, 25, 939-951; published May 18, 2015.
Chiron D, et al. Cancer Discovery, 2014, 4, 1022-1035.
Woyach JA, el al. New England Journal of Medicine, 2014, 370, 2286-2294.
Gunderson AJ, et al. Cancer Discov. 2016, 6, 270-285, published online Dec. 29, 2015.
Mulligan, LM. Nat Rev Cancer. 2014, 14(3):173-86.
Fujita-Sato, S., et al. Enhanced MET Translation and Signaling Sustains K-Ras-Driven Proliferation under Anchorage-Independent Growth Conditions. Cancer Res. 2015, 75, 2851-2862.
Song N, et al. Cetuximab-induced MET activation acts as a novel resistance mechanism in colon cancer cells. Int J Mol Sci. 2014, 15, 5838-5851.
Ries CH, et al. Targeting tumor-associated macrophages with anti-CSFIR antibody reveals a strategy for cancer therapy. Cancer Cell. 2014, 25, 846-859.

(56) References Cited

OTHER PUBLICATIONS

Apicella et al., "Dual MET/EGFR therapy leads to complete response and resistance prevention in a MET-amplified gastroesophageal xenopatient cohort", Oncogene (2017) 36, 1200-1210. Published online Aug. 15, 2016.

Baldanzi et al., "Physiological Signaling and Structure of the HGF Receptor MET", Biomedicines 2015, 3, 1-31. First published Dec. 31, 2014.

Bender et al., "Recurrent MET fusion genes represent a drug target in pediatric glioblastoma", Nature Medicine 22, 1314-1320 (2016). Published online Oct. 17, 2016.

Heynen et al., "Resistance to targeted cancer drugs through hepatocyte growth factor signaling", Cell Cycle, 2014, 13:24, 3808-3817. Accepted Nov. 11, 2014.

Kato et al., "RET Aberrations in Diverse Cancers: Next-Generation Sequencing of 4,871 Patients", Clin Cancer Res., Apr. 15, 2017; 23(8): 1988-1997. Published online Sep. 28, 2016.

Ko et al., "MET/HGF pathway activation as a paradigm of resistance to targeted therapies", Ann Transl Med., Jan. 2017; 5(1):4.

PCT Search Report and Written Opinion prepared for PCT/US2018/015150, completed Mar. 14, 2018.

Karachaliou, Niki, et al., "Common Co-activation of AXL and CDCP1 in EGFR-mutation-positive Non-Small Cell Lung Cancer Associated With Poor Prognosis," Mar. 1, 2018, EBioMedicine, vol. 29, pp. 112-127.

Gargalionis, Antonios N., et al., "The molecular rationale of Src inhibition in colorectal carcinomas : Src in colorectal cancer," May 1, 2014, International Journal of Cancer, vol. 134, No. 9, pp. 2019-2029.

\* cited by examiner

COMBINATION THERAPY INVOLVING DIARYL MACROCYCLIC COMPOUNDS

CROSS-REFERENCE TO RELATED APPLICATIONS

This application is a national stage entry under 35 USC § 371 of PCT International Application Number PCT/US2018/015150, filed Jan. 25, 2018, which claims priority under 35 U.S.C. § 119(e) to U.S. Provisional Application Ser. No. 62/450,455 filed on Jan. 25, 2017 and U.S. Provisional Application Ser. No. 62/619,165 filed on Jan. 19, 2018, the entire disclosures of both of which are incorporated herein by reference.

TECHNICAL FIELD

The present disclosure relates to methods and compositions for treating cancer with a diaryl macrocycle in combination with at least one other cancer therapeutic, such as an EGFR inhibitor.

BACKGROUND

EGFR is expressed in several solid malignancies, including NSCLC, HNSCC, malignant glioma and colorectal cancer, and abnormal or deregulated EGFR activity is known to contribute to numerous tumorigenic processes. Lung cancer remains the leading cause of cancer death in industrialized countries. Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. About 75 percent of lung cancer cases are categorized as non-small cell lung cancer (e.g., adenocarcinomas), and the other 25 percent are small cell lung cancer. For patients with advanced disease, chemotherapy provides a modest benefit in survival, but at the cost of significant toxicity, underscoring the need for therapeutic agents that are specifically targeted to the critical genetic lesions that direct tumor growth (Schiller J H et al., N Engl J Med, 346: 92-98, 2002).

Mutations that lead to EGFR overexpression (known as upregulation) or overactivity have been associated with a number of cancers, including lung cancer, anal cancers and glioblastoma multiforme. Mutations, amplifications or misregulations of EGFR or family members are implicated in about 30% of all epithelial cancers. Consequently, mutations of EGFR have been identified in several types of cancer, and has led to the development of anticancer therapeutics directed against EGFR, using two approaches: (1) targeted monoclonal antibodies (mABs) that prevent the binding of ligands to EGFR, and (2) small molecule tyrosine kinase inhibitors (TKIs) that block the intracellular catalytic activity of the receptor. Protein kinases are key regulators for cell growth, proliferation and survival. Genetic and epigenetic alterations accumulate in cancer cells leading to abnormal activation of signal transduction pathways which drive malignant processes. (Manning, G.; Whyte, D. B.; Martinez, R.; Hunter, T.; Sudarsanam, S. The protein kinase complement of the human genome. *Science* 2002, 298, 1912-1934). Pharmacological inhibition of these signaling pathways presents promising intervention opportunities for targeted cancer therapies. (Sawyers, C. Targeted cancer therapy. *Nature* 2004, 432, 294-297).

First generation small molecule HER TKIs include gefitinib (Iressa®) and erlotinib (Tarceva®), both binding reversibly to the EGFR. Gefitinib is indicated in all lines of treatment of advanced NSCLC harboring EGFR mutations in the tumor and erlotinib is indicated as treatment of advanced NSCLC after prior chemotherapy, but in development in all lines of EGFR mutation positive NSCLC. These new drugs reversibly target the EGFR kinase domain.

Second generation small molecule TKIs have been designed as irreversible EGFR inhibitors which bind irreversibly to EGFR kinase domain, preferably to cysteine 797 of EGFR. Despite initial response in patients with EGFR mutations, acquired resistance often develops after a median of approximately 12 months. The consensus definition of acquired resistance includes patients who had previous treatment with a single-agent EGFR-TKI (e.g., gefitinib or erlotinib); either or both of the following: a tumor that harbors an EGFR mutation known to be associated with drug sensitivity (i.e., G719X, exon 19 deletion, L858R, L861Q) or objective clinical benefit from treatment with an EGFR-TKI; systemic progression of disease applying RECIST criteria known in the art, while on continuous treatment with EGFR directed treatment for at least 24 weeks.

Despite the success of the first and second generations of EGFR inhibitors in targeted NSCLC therapies, the duration of clinical response is limited by the inevitable development of acquired drug resistance. In addition to the primary EGFR mutations (associated with erlotinib and gefitinib sensitivity), approximately half of the patients with acquired EGFR-TKI resistance have a second EGFR mutation (T790M) in the ATP-binding pocket of the tyrosine kinase that may alter receptor affinity in favor of ATP. These second mutations enable the cancer cells to continue signaling via mutant EGFR, suggesting that in a proportion of patients with acquired resistance to EGFR-TKIs, tumor growth and proliferation remains dependent on EGFR. Other intrinsic or acquired resistance mechanisms include the upregulation of bypass signalings (such as AXL, MET, ERBb2, etc), activating mutations in the downstream pathways (PI3K, AKT, MEK, RAF), low levels of mRNA or polymorphisms of the pro-apoptotic protein BIM, induction of a transcription programme for EMT and phenotypical changes, or induction of elevated tumour PD-L1 levels. (Morgillo F, Della Corte C M, Fasano M, et al. Mechanisms of resistance to EGFR-targeted drugs: lung cancer. ESMO Open 2016; 1: e000060)

There is a significant medical need in the art for a satisfactory treatment of cancer driven by EGFR. In addition to the single-agent targeted therapies strategies outlined above in first line and for overcoming the non-responsiveness exhibited by resistant cancers, combination treatments may also provide promise.

SUMMARY

It has been discovered that the combination of an EGFR inhibitor and a triple inhibitor of FAK, SRC and JAK2 provides a robust response in cancers driven by EGFR.

In one aspect, the disclosure provides a method for treating cancer in a host animal, the method comprising the step of administering to the host animal a therapeutically effective amount of a compound that inhibits FAK, SRC and JAK2, in combination with a therapeutically effective amount of at least one additional anti-cancer agent. In some embodiments, the additional anti-cancer agent is an EGFR inhibitor, or a pharmaceutically acceptable salt thereof.

In another aspect, the disclosure provides a compound that inhibits FAK, SRC and JAK2, or a pharmaceutically acceptable salt thereof, for use in the treatment of cancer in a patient, in combination with a therapeutically effective amount of at least one additional anti-cancer agent. In some embodiments, the additional anti-cancer agent is an EGFR inhibitor, or a pharmaceutically acceptable salt thereof.

In another aspect, the disclosure provides use of a compound that inhibits FAK, SRC and JAK2, or a pharmaceutically acceptable salt thereof, in the preparation of a medicament comprising a therapeutically effective amount of the compound, for treating cancer in a patient in combination with a therapeutically effective amount of at least one additional anti-cancer agent. In some embodiments, the additional anti-cancer agent is an EGFR inhibitor, or a pharmaceutically acceptable salt thereof.

In another aspect, the disclosure provides a composition comprising a compound that inhibits FAK, SRC and JAK2, or a pharmaceutically acceptable salt thereof, in a therapeutically effective amount, for use in the treatment of cancer in a patient, in combination with a therapeutically effective amount of at least one additional anti-cancer agent. In some embodiments, the additional anti-cancer agent is an EGFR inhibitor, or a pharmaceutically acceptable salt thereof.

In another aspect, the disclosure provides a medicament comprising a compound that inhibits FAK, SRC and JAK2, or a pharmaceutically acceptable salt thereof, combined with an EGFR inhibitor, or a pharmaceutically acceptable salt thereof, in fixed or free combination.

In another aspect, the disclosure provides a synergistic composition of a compound that inhibits FAK, SRC and JAK2 and an EGFR inhibitor, where the two components come into contact with each other at a locus.

In another aspect, the disclosure provides a synergistic composition of a compound that inhibits FAK, SRC and JAK2 and an EGFR inhibitor, where the two components come into contact with each other only in the human body.

In some embodiments the compound that inhibits FAK, SRC and JAK2 is of the formula I or II

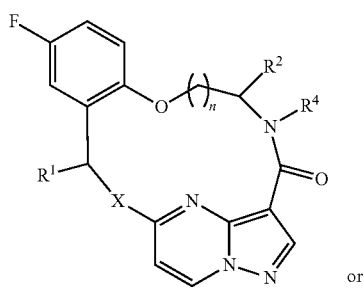

I

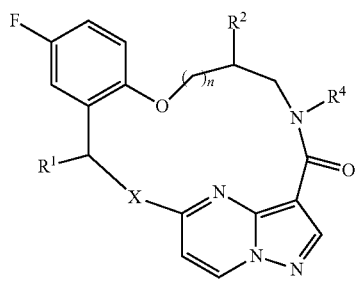

II wherein
X is $NR^3$ or $CHR^3$;
each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

In some embodiments the compound that inhibits FAK, SRC and JAK2 is of the formula I-a or II-a

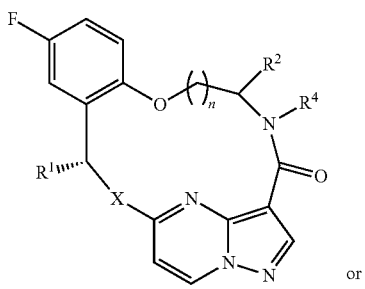

I-a or

-continued

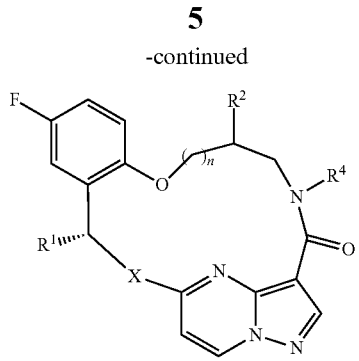

II-a wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

In some embodiments the compound that inhibits FAK, SRC and JAK2 is of the formula I-b or II-b

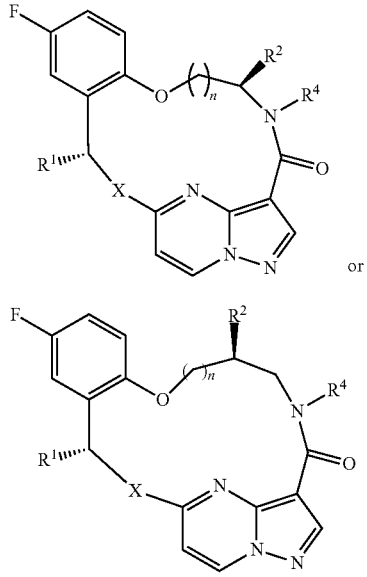

wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

In some embodiments of the above aspects, the compound that inhibits FAK, SRC and JAK2 is of the formula

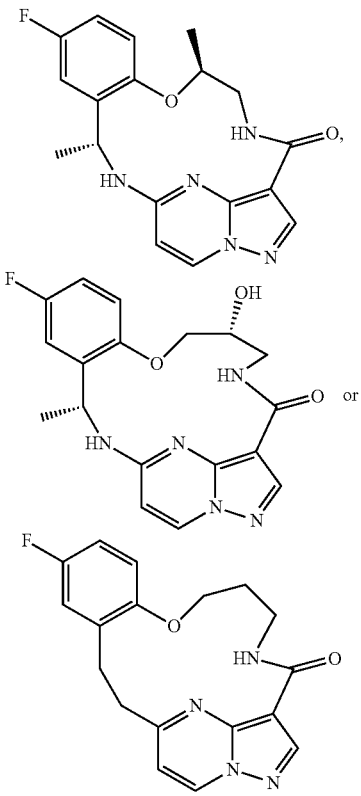

or a pharmaceutically acceptable salt thereof.

In some embodiments of the above aspects, the EGFR inhibitor is an antibody or a small molecule inhibitor. In some embodiments of the above aspects, the EGFR inhibitor is an antibody. In some embodiments of the above aspects, the antibody is cetuximab, necitumumab or panitumumab. In some embodiments of the above aspects, the EGFR inhibitor is a small molecule inhibitor. In some embodiments of the above aspects, the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib, PF-06747775, rociletinib, vandetanib, WZ 3146, WZ 4002, WZ 8040, or pharmaceutically acceptable salts thereof.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A method for treating cancer in a host animal, the method comprising the step of administering to the host animal a therapeutically effective amount of a compound that inhibits FAK, SRC and JAK2, in combination with a therapeutically effective amount of at least one additional anti-cancer agent.

2. The method of clause 1, wherein the compound that inhibits FAK, SRC and JAK2 is of the formula I or II

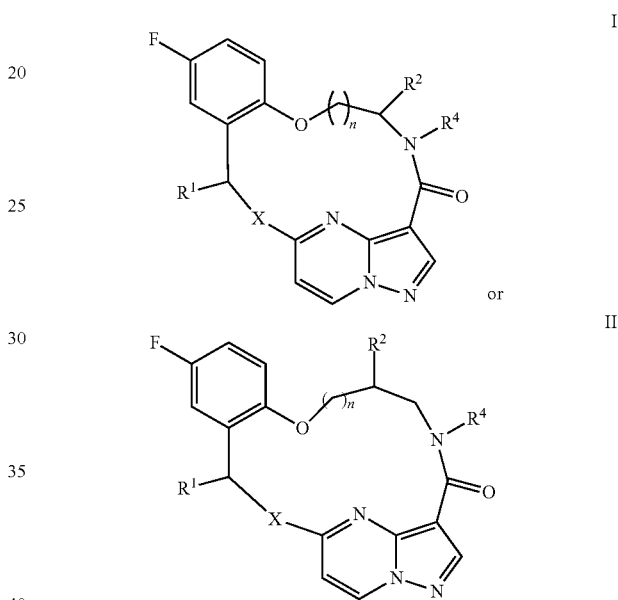

wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OR$^5$, —C(O)OR$^5$ or —C(O)NR$^5$R$^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, —C$_3$-C$_6$ cycloalkyl, or 3- to 7-membered heterocycloalkyl;

R$^3$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^5$;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^5$ and R$^6$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and n is 0 or 1;

or a pharmaceutically acceptable salt thereof.

3. The method of clause 1 or 2, wherein the compound that inhibits FAK, SRC and JAK2 is a compound of the formula

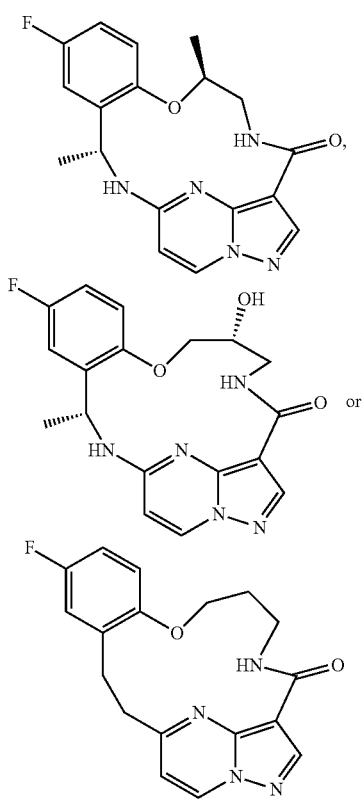

or a pharmaceutically acceptable salt thereof.

4. The method of clause 1 to 3, wherein the cancer is selected from the group consisting of ALCL, NSCLC, neuroblastoma, inflammatory myofibroblastic tumor, adult renal cell carcinoma, pediatric renal cell carcinoma, breast cancer, ER$^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

5. The method of any one of clauses 1 to 4, wherein the cancer is non-small cell lung cancer, metastatic non-small cell lung cancer, head and neck squamous cell carcinoma, metastatic head and neck squamous cell carcinoma, colorectal cancer, metastatic colorectal cancer, pancreatic cancer, or metastatic pancreatic cancer.

6. The method of clause 4, wherein the cancer is non-small cell lung cancer.

7. The method of clause 4, wherein the cancer is colorectal cancer.

8. The method of clause 4, wherein the cancer is pancreatic cancer.

9. The method of clause 4, wherein the cancer is triple negative breast.

10. The method of any one of clauses 1 to 9, wherein the additional anti-cancer agent is an EGFR inhibitor, or a pharmaceutically acceptable salt thereof.

11. The method of any one of clauses 1 to 10, wherein the additional anti-cancer agent is an antibody of EGFR or a small molecule inhibitor of EGFR.

12. The method of any one of clauses 1 to 10, wherein the additional anti-cancer agent is an antibody of EGFR.

13. The method of clause 13, wherein the antibody is cetuximab, necitumumab or panitumumab.

14. The method of any one of clauses 1 to 10, wherein the additional anti-cancer agent is a small molecule inhibitor of EGFR.

15. The method of clause 14, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, politinib, PF-06747775, rociletinib, vandetanib, or pharmaceutically acceptable salts thereof.

16. The method of any one of clauses 1 to 9, wherein the additional anti-cancer agent is gefitinib, or a pharmaceutically acceptable salt thereof.

17. The method of any one of clauses 1 to 9, wherein the additional anti-cancer agent is osimertinib, or a pharmaceutically acceptable salt thereof.

18. The method of any one of clauses 1 to 9, wherein the additional anti-cancer agent is erlotinib, or a pharmaceutically acceptable salt thereof.

18a. The method of any one of clauses 1 to 9, wherein the additional anti-cancer agent is icotinib, or a pharmaceutically acceptable salt thereof.

19. A compound that inhibits FAK, SRC and JAK2, or a pharmaceutically acceptable salt thereof, for use in the treatment of cancer in a patient, in combination with a therapeutically effective amount of at least one additional anti-cancer agent.

20. The compound of clause 19, wherein the compound that inhibits FAK, SRC and JAK2 is of the formula I or II

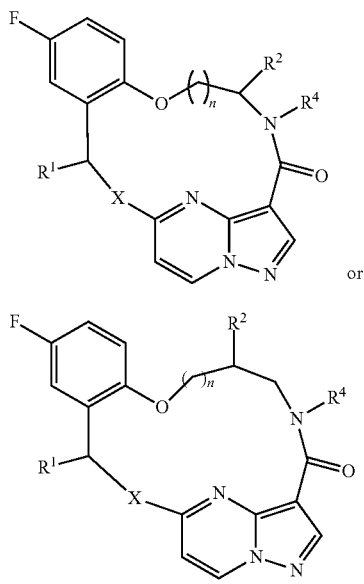

wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

21. The compound of clause 19, wherein the compound that inhibits FAK, SRC and JAK2 is a compound of the formula

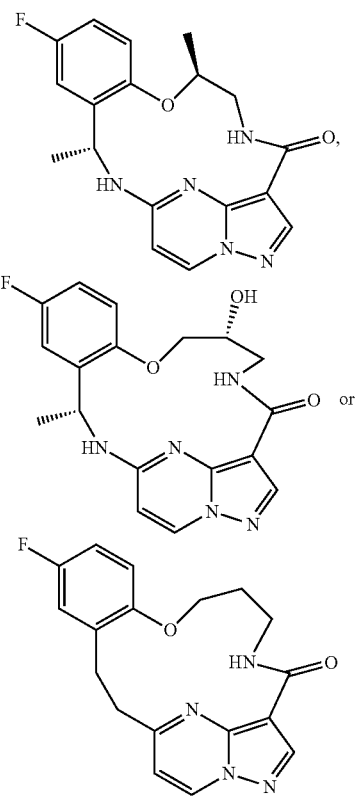

or a pharmaceutically acceptable salt thereof.

22. The compound of any one of clauses 19 to 21, wherein the cancer is selected from the group consisting of ALCL, NSCLC, neuroblastoma, inflammatory myofibroblastic tumor, adult renal cell carcinoma, pediatric renal cell carcinoma, breast cancer, ER$^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

23. The compound of any one of clauses 19 to 21, wherein the cancer is non-small cell lung cancer.

24. The compound of any one of clauses 19 to 21, wherein the cancer is colorectal cancer.

25. The compound of any one of clauses 19 to 21, wherein the cancer is pancreatic cancer.

26. The compound of any one of clauses 19 to 21, wherein the cancer is triple negative breast.

27. The compound of any one of clauses 19 to 21, wherein the cancer is head and neck squamous cell carcinoma.

28. The compound of any one of clauses 19 to 27, wherein the additional anti-cancer agent is an EGFR inhibitor, or a pharmaceutically acceptable salt thereof.

29. The compound of any one of clauses 19 to 27, wherein the additional anti-cancer agent is an antibody of EGFR or a small molecule inhibitor of EGFR.

30. The compound of any one of clauses 19 to 27, wherein the additional anti-cancer agent is an antibody of EGFR.

31. The compound of clause 30, wherein the antibody is cetuximab, necitumumab or panitumumab.

32. The compound of any one of clauses 19 to 27, wherein the additional anti-cancer agent is a small molecule inhibitor of EGFR.

33. The compound of clause 32, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib, PF-06747775, rociletinib, vandetanib, or pharmaceutically acceptable salts thereof.

34. The compound of any one of clauses 19 to 27, wherein the additional anti-cancer agent is gefitinib, or a pharmaceutically acceptable salt thereof.

35. The compound of any one of clauses 19 to 27, wherein the additional anti-cancer agent is osimertinib, or a pharmaceutically acceptable salt thereof.

36. The compound of any one of clauses 19 to 27, wherein the additional anti-cancer agent is erlotinib, or a pharmaceutically acceptable salt thereof.

36a. The compound of any one of clauses 19 to 27, wherein the additional anti-cancer agent is icotinib, or a pharmaceutically acceptable salt thereof.

37. Use of a compound that inhibits FAK, SRC and JAK2, or a pharmaceutically acceptable salt thereof, in the preparation of a medicament comprising a therapeutically effective amount of the compound, for treating cancer in a patient in combination with a therapeutically effective amount of at least one additional anti-cancer agent.

38. The compound of clause 37, wherein the compound that inhibits FAK, SRC and JAK2 is of the formula I or II

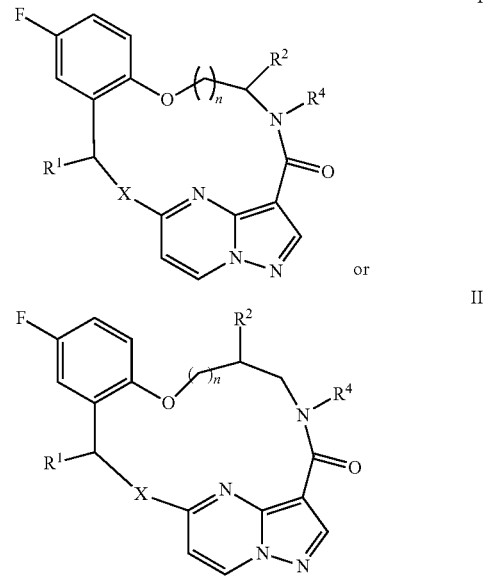

wherein
X is $NR^3$ or $CHR^3$;
each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)N(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^5$ and R$^6$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and n is 0 or 1;

or a pharmaceutically acceptable salt thereof.

39. The use of clause 37, wherein the compound that inhibits FAK, SRC and JAK2 is a compound of the formula

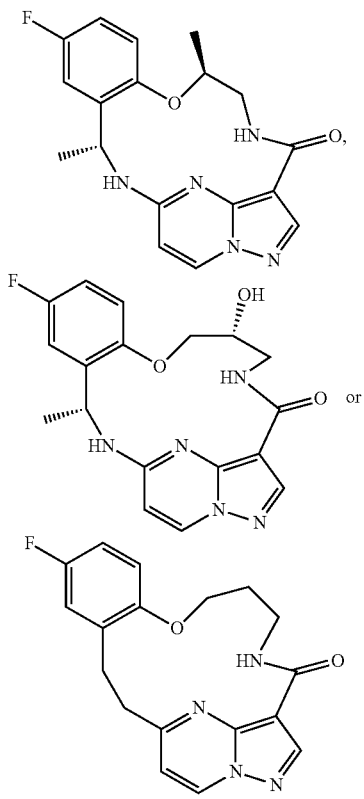

or a pharmaceutically acceptable salt thereof.

40. The use of any one of clauses 37 to 39, wherein the cancer is selected from the group consisting of ALCL, NSCLC, neuroblastoma, inflammatory myofibroblastic tumor, adult renal cell carcinoma, pediatric renal cell carcinoma, breast cancer, ER$^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

41. The use of any one of clauses 37 to 40, wherein the cancer is non-small cell lung cancer.

42. The use of any one of clauses 37 to 40, wherein the cancer is colorectal cancer.

43. The use of any one of clauses 37 to 40, wherein the cancer is pancreatic cancer.

44. The use of any one of clauses 37 to 40, wherein the cancer is triple negative breast.

45. The use of any one of clauses 37 to 40, wherein the cancer is head and neck squamous cell carcinoma.

46. The use of any one of clauses 37 to 45, wherein the additional anti-cancer agent is an EGFR inhibitor, or a pharmaceutically acceptable salt thereof.

47. The use of any one of clauses 37 to 45, wherein the additional anti-cancer agent is an antibody of EGFR or a small molecule inhibitor of EGFR.

48. The use of any one of clauses 37 to 45, wherein the additional anti-cancer agent is an antibody of EGFR.

49. The use of clause 48, wherein the antibody is cetuximab, necitumumab or panitumumab.

50. The use of any one of clauses 37 to 45, wherein the additional anti-cancer agent is a small molecule inhibitor of EGFR.

51. The use of clause 50, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib, PF-06747775, rociletinib, vandetanib, or pharmaceutically acceptable salts thereof.

52. The use of any one of clauses 37 to 45, wherein the additional anti-cancer agent is gefitinib, or a pharmaceutically acceptable salt thereof.

53. The use of any one of clauses 37 to 45, wherein the additional anti-cancer agent is osimertinib, or a pharmaceutically acceptable salt thereof.

54. The use of any one of clauses 37 to 45, wherein the additional anti-cancer agent is erlotinib, or a pharmaceutically acceptable salt thereof.

54a. The use of any one of clauses 37 to 45, wherein the additional anti-cancer agent is icotinib, or a pharmaceutically acceptable salt thereof.

55. A composition comprising a compound that inhibits FAK, SRC and JAK2, or a pharmaceutically acceptable salt thereof, in a therapeutically effective amount, for use in the treatment of cancer in a patient, in combination with a therapeutically effective amount of at least one additional anti-cancer agent.

56. The composition of clause 55, wherein the compound that inhibits FAK, SRC and JAK2 is of the formula I or II

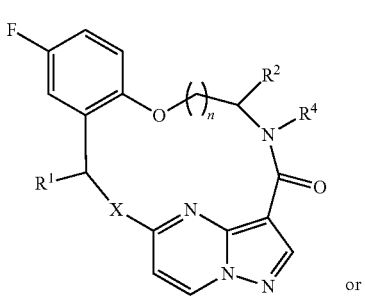

I or

17
-continued

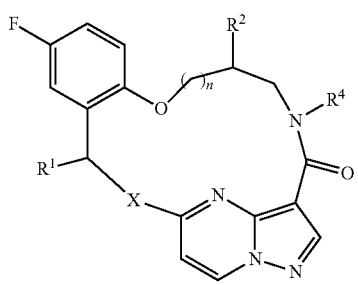

II wherein
X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —C(O)$OR^5$ or —C(O)$NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)O$C_1$-$C_6$ alkyl, —C(O)$NH_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_{2N}$($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —NH($C_1$-$C_6$ alkyl), —N($C_1$-$C_6$ alkyl)$_2$, —$CO_2H$, —C(O)O$C_1$-$C_6$ alkyl, —C(O)$NH_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

57. The composition of clause 55, wherein the compound that inhibits FAK, SRC and JAK2 is a compound of the formula

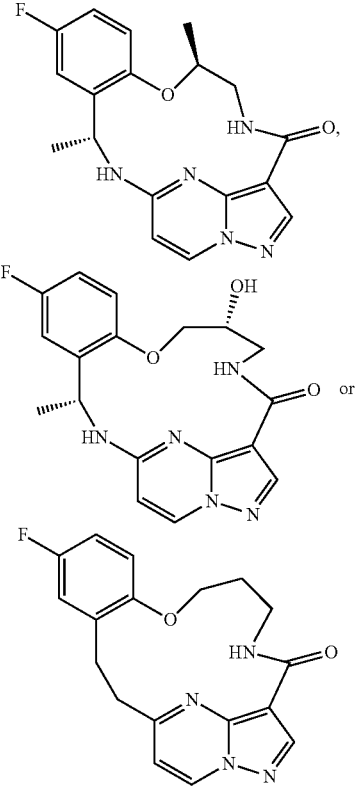

or a pharmaceutically acceptable salt thereof.

58. The composition of any one of clauses 55 to 57, wherein the cancer is selected from the group consisting of ALCL, NSCLC, neuroblastoma, inflammatory myofibroblastic tumor, adult renal cell carcinoma, pediatric renal cell carcinoma, breast cancer, $ER^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

59. The composition of any one of clauses 55 to 58, wherein the cancer is non-small cell lung cancer.

60. The composition of any one of clauses 55 to 58, wherein the cancer is colorectal cancer.

61. The composition of any one of clauses 55 to 58, wherein the cancer is pancreatic cancer.

62. The composition of any one of clauses 55 to 58, wherein the cancer is triple negative breast.

63. The composition of any one of clauses 55 to 58, wherein the cancer is head and neck squamous cell carcinoma.

64. The composition of any one of clauses 55 to 63, wherein the additional anti-cancer agent is an EGFR inhibitor, or a pharmaceutically acceptable salt thereof.

65. The composition of any one of clauses 55 to 63, wherein the additional anti-cancer agent is an antibody of EGFR or a small molecule inhibitor of EGFR.

66. The composition of any one of clauses 55 to 63, wherein the additional anti-cancer agent is an antibody of EGFR.

67. The composition of clause 66, wherein the antibody is cetuximab, necitumumab or panitumumab.

68. The composition of any one of clauses 55 to 63, wherein the additional anti-cancer agent is a small molecule inhibitor of EGFR.

69. The composition of clause 68, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, politinib, PF-06747775, rociletinib, vandetanib, or pharmaceutically acceptable salts thereof.

70. The composition of any one of clauses 55 to 63, wherein the additional anti-cancer agent is gefitinib, or a pharmaceutically acceptable salt thereof.

71. The composition of any one of clauses 55 to 63, wherein the additional anti-cancer agent is osimertinib, or a pharmaceutically acceptable salt thereof.

72. The composition of any one of clauses 55 to 63, wherein the additional anti-cancer agent is erlotinib, or a pharmaceutically acceptable salt thereof.

72a. The composition of any one of clauses 55 to 63, wherein the additional anti-cancer agent is icotinib, or a pharmaceutically acceptable salt thereof.

73. A medicament comprising a compound that inhibits FAK, SRC and JAK2, or a pharmaceutically acceptable salt thereof, combined with an EGFR inhibitor, or a pharmaceutically acceptable salt thereof, in fixed or free combination.

74. The medicament of clause 73, wherein the compound that inhibits FAK, SRC and JAK2 is of the formula I or II

I or

II wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$^2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

75. The medicament of clause 73, wherein the compound that inhibits FAK, SRC and JAK2 is a compound of the formula

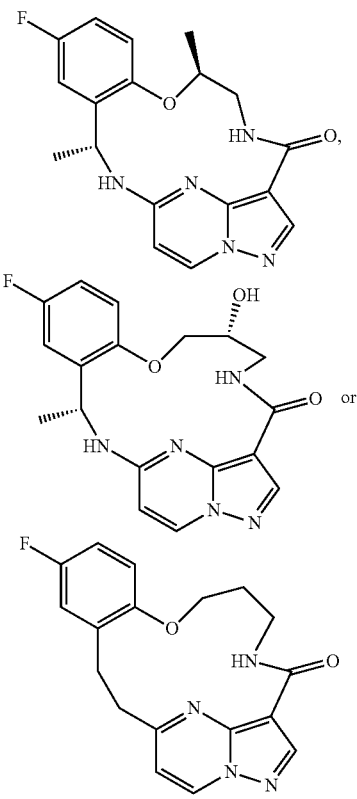

or a pharmaceutically acceptable salt thereof.

76. The medicament of any one of clauses 73 to 75, wherein medicament provides a synergistic effect on a cancer selected from the group consisting of ALCL, NSCLC, neuroblastoma, inflammatory myofibroblastic tumor, adult renal cell carcinoma, pediatric renal cell carcinoma, breast cancer, ER+ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

77. The medicament of any one of clauses 73 to 76, wherein the cancer is non-small cell lung cancer.

78. The medicament of any one of clauses 73 to 76, wherein the cancer is colorectal cancer.

79. The medicament of any one of clauses 73 to 76, wherein the cancer is pancreatic cancer.

80. The medicament of any one of clauses 73 to 76, wherein the cancer is triple negative breast.

81. The medicament of any one of clauses 73 to 76, wherein the cancer is head and neck squamous cell carcinoma.

82. The medicament of any one of clauses 73 to 81, wherein the EGFR inhibitor is an antibody or a small molecule inhibitor.

83. The medicament of any one of clauses 73 to 81, wherein the EGFR inhibitor is an antibody.

84. The medicament of clause 83, wherein the antibody is cetuximab, necitumumab or panitumumab.

85. The medicament of any one of clauses 73 to 81, wherein the EGFR inhibitor is a small molecule inhibitor.

86. The medicament of clause 85, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib. PF-06747775, rociletinib, vandetanib, or pharmaceutically acceptable salts thereof.

87. The medicament of any one of clauses 73 to 81, wherein the EGFR inhibitor is gefitinib, or a pharmaceutically acceptable salt thereof.

88. The medicament of any one of clauses 73 to 81, wherein the EGFR inhibitor is osimertinib, or a pharmaceutically acceptable salt thereof.

89. The medicament of any one of clauses 73 to 81, wherein the EGFR inhibitor is erlotinib, or a pharmaceutically acceptable salt thereof.

89a. The medicament of any one of clauses 73 to 81, wherein the additional anti-cancer agent is icotinib, or a pharmaceutically acceptable salt thereof.

90. A synergistic composition of a compound that inhibits FAK, SRC and JAK2 and an EGFR inhibitor, where the two components come into contact with each other at a locus.

91. The synergistic composition of clause 90, wherein the compound that inhibits FAK, SRC and JAK2 is of the formula I or II

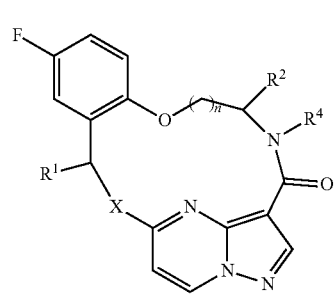

or

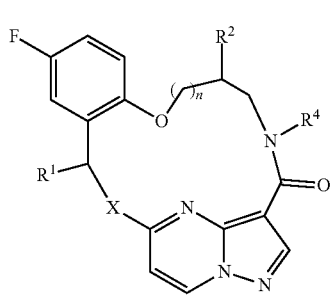

wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

92. The synergistic composition of clause 90, wherein the compound that inhibits FAK, SRC and JAK2 is a compound of the formula

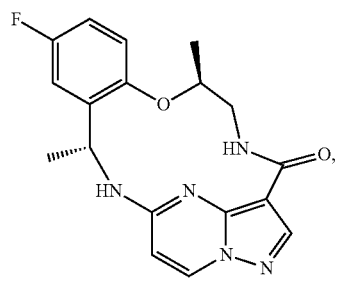

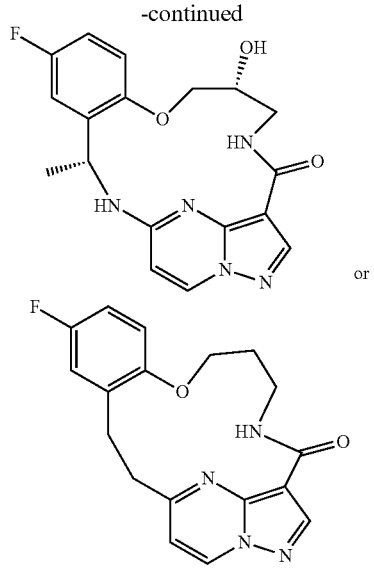

or a pharmaceutically acceptable salt thereof.

93. The synergistic composition of any one of clauses 90 to 92, wherein the locus is a cancer or a cancer cell.

94. The synergistic composition of any one of clauses 90 to 92, wherein the locus is a cancer selected from the group consisting of ALCL, NSCLC, neuroblastoma, inflammatory myofibroblastic tumor, adult renal cell carcinoma, pediatric renal cell carcinoma, breast cancer, $ER^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

95. The synergistic composition of any one of clauses 90 to 93, wherein the cancer is non-small cell lung cancer.

96. The synergistic composition of any one of clauses 90 to 93, wherein the cancer is colorectal cancer.

97. The synergistic composition of any one of clauses 90 to 93, wherein the cancer is pancreatic cancer.

98. The synergistic composition of any one of clauses 90 to 93, wherein the cancer is triple negative breast.

99. The synergistic composition of any one of clauses 90 to 93, wherein the cancer is head and neck squamous cell carcinoma.

100. The synergistic composition of any one of clauses 90 to 99, wherein the EGFR inhibitor is an antibody or a small molecule inhibitor.

101. The synergistic composition of any one of clauses 90 to 99, wherein the EGFR inhibitor is an antibody.

102. The synergistic composition of clause 101, wherein the antibody is cetuximab, necitumumab or panitumumab.

103. The synergistic composition of any one of clauses 90 to 99, wherein the EGFR inhibitor is a small molecule inhibitor.

104. The synergistic composition of clause 103, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib, PF-06747775, rociletinib, vandetanib, or pharmaceutically acceptable salts thereof.

105. The synergistic composition of any one of clauses 90 to 99, wherein the EGFR inhibitor is gefitinib, or a pharmaceutically acceptable salt thereof.

106. The synergistic composition of any one of clauses 90 to 99, wherein the EGFR inhibitor is osimertinib, or a pharmaceutically acceptable salt thereof.

107. The synergistic composition of any one of clauses 90 to 99, wherein the EGFR inhibitor is erlotinib, or a pharmaceutically acceptable salt thereof.

107a. The synergistic composition of any one of clauses 90 to 99, wherein the additional anti-cancer agent is icotinib, or a pharmaceutically acceptable salt thereof.

108. A synergistic composition of a compound that inhibits FAK, SRC and JAK2 and an EGFR inhibitor, where the two components come into contact with each other only in the human body.

109. The synergistic composition of clause 90, wherein the compound that inhibits FAK, SRC and JAK2 is of the formula I or II

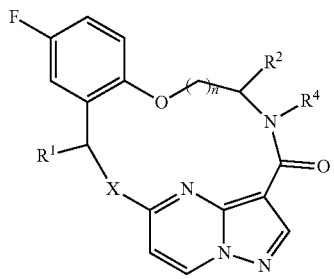

I or

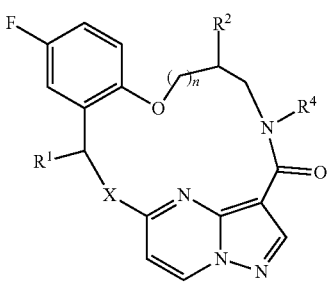

II wherein

X is NR$^3$ or CHR$^3$;

each of R$^1$ and R$^2$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —OR$^5$, —C(O)OR$^5$ or —C(O)NR$^5$R$^6$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, —C$_3$-C$_6$ cycloalkyl, or 3- to 7-membered heterocycloalkyl;

R$^3$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^5$;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

each R$^5$ and R$^6$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or heteroaryl; and n is 0 or 1;

or a pharmaceutically acceptable salt thereof.

110. The synergistic composition of clause 108, wherein the compound that inhibits FAK, SRC and JAK2 is a compound of the formula

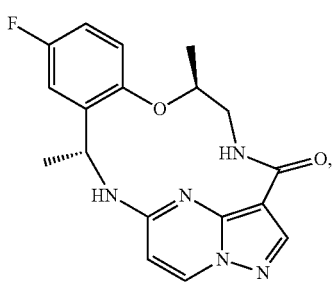

-continued

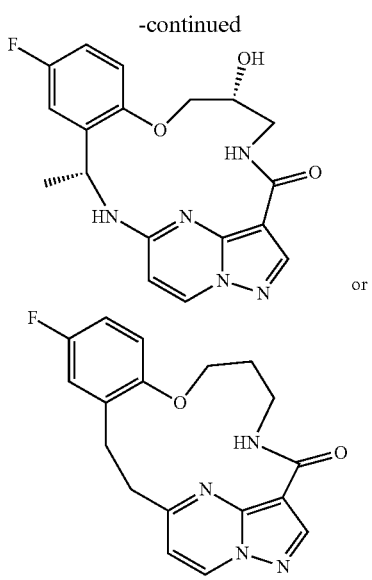

or a pharmaceutically acceptable salt thereof.

111. The synergistic composition of any one of clauses 108 to 110, wherein the EGFR inhibitor is an antibody of EGFR or a small molecule inhibitor of EGFR.

112. The synergistic composition of clause 111, wherein the EGFR inhibitor is an antibody.

113. The synergistic composition of clause 112, wherein the antibody is cetuximab, necitumumab or panitumumab.

114. The synergistic composition of clause 111, wherein the EGFR inhibitor is a small molecule inhibitor.

115. The synergistic composition of clause 114, wherein the small molecule inhibitor is afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib, PF-06747775, rociletinib, vandetanib, or pharmaceutically acceptable salts thereof.

116. The synergistic composition of clause 114, wherein the EGFR inhibitor is gefitinib, or a pharmaceutically acceptable salt thereof.

117. The synergistic composition of clause 114, wherein the EGFR inhibitor is osimertinib, or a pharmaceutically acceptable salt thereof.

118. The synergistic composition of clause 114, wherein the EGFR inhibitor is erlotinib, or a pharmaceutically acceptable salt thereof.

119. The synergistic composition of clause 114, wherein the additional anti-cancer agent is icotinib, or a pharmaceutically acceptable salt thereof.

DETAILED DESCRIPTION

Figure 1A:
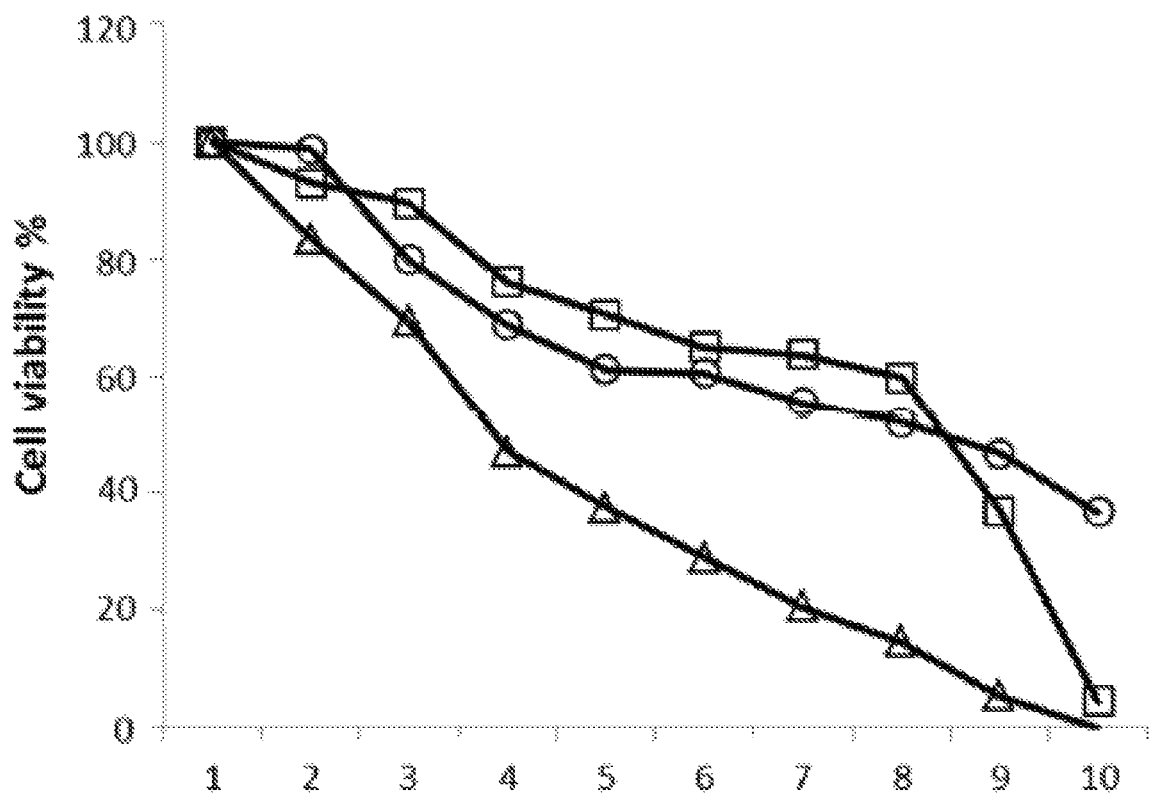
FIG. 1a shows cell viability % of the EGFR inhibitor gefitinib, Compound 1, and gefitinib and Compound 1 in PC9 cells at various doses. (○) gefitinib; (□) Compound 1; (Δ) gefitinib+Compound 1.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

As used herein, the term "therapeutically effective amount" refers to that amount of active compound or pharmaceutical agent that elicits the biological or medicinal response in a patient, which includes alleviation of the symptoms of the disease or disorder being treated. In one aspect, the therapeutically effective amount is that which may treat or alleviate the disease or symptoms. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

As used herein, the term "disease" includes, but is not limited to, cancer, pain, psoriasis, rheumatoid arthritis, polycythemia vera, essential thrombocythemia, ulcerative colitis, and myeloid metaplasia with myelofibrosis.

As used herein, the term "cancer" includes, but is not limited to, ALCL, lung cancer, such as non-small cell lung cancer (NSCLC), including adenocarcinoma, lung squamous cell carcinoma, large cell carcinoma, and large cell neuroendocrine tumors, small cell lung cancer (SCLC), neuroblastoma, inflammatory myofibroblastic tumor, adult renal cell carcinoma, pediatric renal cell carcinoma, breast cancer, such as triple negative breast cancer, triple positive breast cancer, ER$^+$ breast cancer, and HER2-overexpressing breast cancer, colonic adenocarcinoma, glioblastoma, glioblastoma multiforme, thyroid cancer, such as anaplastic thyroid cancer, cholangiocarcinoma, ovarian cancer, gastric cancer, such as gastric adenocarcinoma, colorectal cancer (CRC), inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cancer, such as skin cutaneous melanoma, head and neck squamous cell carcinoma (HNSCC), pediatric glioma CML, prostate cancer, ovarian serous cystadenocarcinoma, skin cutaneous melanoma, castrate-resistant prostate cancer, Hodgkin lymphoma, and serous and clear cell endometrial cancer. It will be appreciated that the term "cancer" includes both primary cancers or primary tumors and metastatic cancers or metastatic tumors. For example, metastatic NSCLC, metastatic CRC, metastatic pancreatic cancer, metastatic HER2-overexpressing breast cancer, metastatic EGFR-expressing colorectal carcinoma, metastatic HNSCC, and the like. It will be appreciated that the term "cancer" includes cancers that involve the upregulation of certain genes or genetic mutations in certain genes that can lead to disease progression, such up-regulation of epidermal growth factor receptor.

As used herein, the term "EGFR inhibitor" includes, but is not limited to, any compound or agent known in the art to inhibit epidermal growth factor receptor (EGFR, also known as ErbB-1 or HER-1). It will be appreciated that EGFR inhibitor includes targeted agents that exhibit specificity for EGFR or are targeted to cancers that express EGFR. It will be appreciated that a compound or agent that inhibits EGFR can be a biological molecule, such as an antibody (e.g. a monoclonal antibody or mAb), a small molecule drug/inhibitor, or a targeted agent. Examples of suitable EGFR inhibitors include, but are not limited to afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, pelitinib. PF-06747775, rociletinib, vandetanib, WZ 3146, WZ 4002, WZ 8040 and pharmaceutically acceptable salts thereof. See for example, U.S. Pat. Nos. 6,002,008, 7,019,012, 6,251,912, WO 02/50043, WO 2004/074263, WO 2005/037824, WO 2008150118 (specifically the compound of Example 36, 1-(4-(4-(3,4-dichloro-2-fluorophenylamino)-7-methoxyquinazolin-6-yloxy)piperidin-1-yl) prop-2-en-1-one, or salts thereof formed with acidic additives as disclosed in WO 2011155793).

Chemical Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

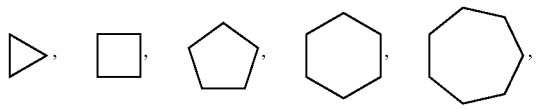

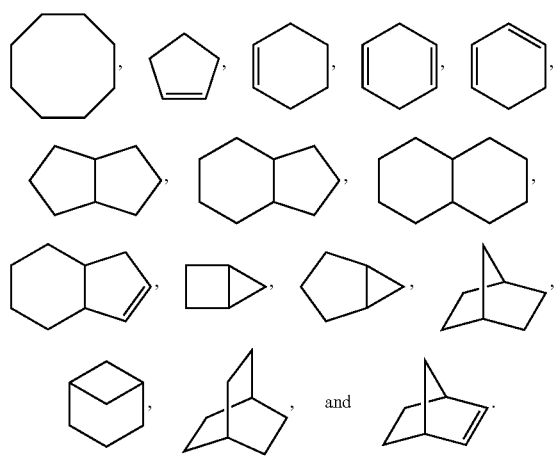

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

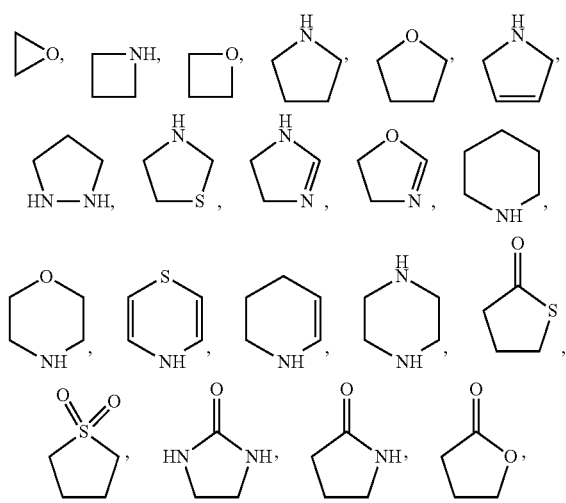

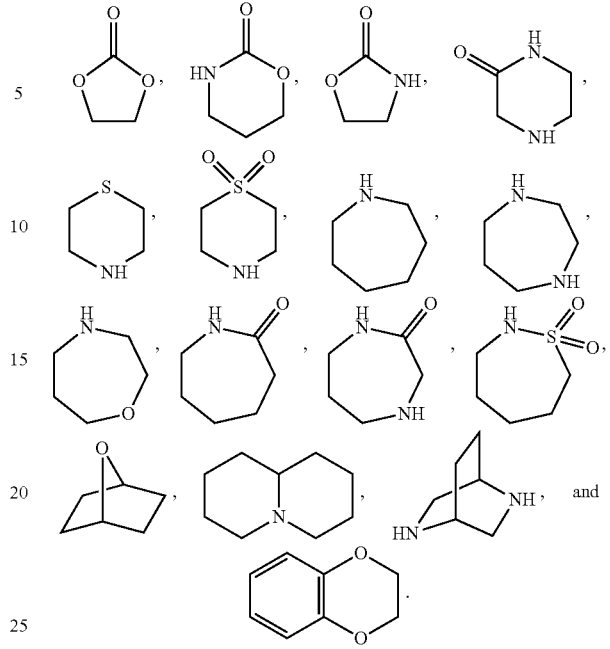

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

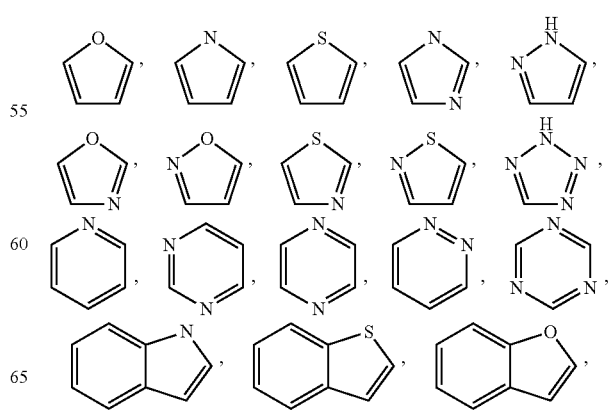

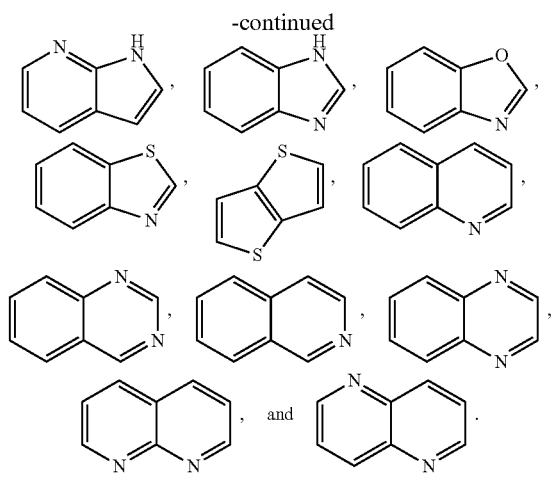

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "∿∿" include both stereoisomers for the carbon atom to which the symbol "∿∿" is attached, specifically both the bonds "━▰" "⋯⋯⋯" are encompassed by the meaning of "∿∿". For example, in some exemplary embodiments, certain compounds provided herein can be described by the formula

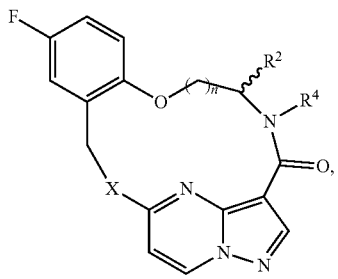

which formula will be understood to encompass compounds having both stereochemical configurations at the relevant carbon atom, specifically in this example

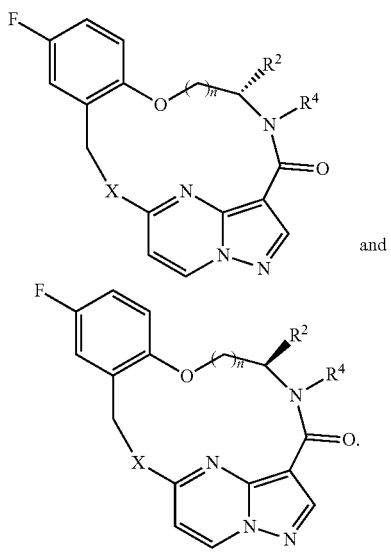

Embodiments

In some embodiments, the methods described herein relate to the treatment of cancer comprising administering to a patient in need of treatment a therapeutically effective amount of a compound that inhibits FAK, SRC and JAK2 in combination with an EGFR inhibitor. It will be appreciated that an inhibitor is any substance that reduces or suppresses the activity of another substance, such as a cell surface receptor (i.e. a receptor tyrosine kinase), or a kinase (i.e. a non-receptor tyrosine kinase). The definition of an "inhibitor" is well known to one of skill in the art, and the use herein of the general term "inhibitor" is understood to be the usual and customary meaning. It will be appreciated that "a compound that inhibits FAK, SRC and JAK2" is a compound that has affinity for all three of the biological targets FAK, SRC and JAK2.

The Janus family of kinases (JAKs) include JAK1, JAK2, JAK3 and TYK2, and are cytoplastic non-receptor tyrosine kinases required for the physiologic signaling of cytokines and growth factors. (Quintas-Cardama A, et al., Nat. Rev. Drug Discov. 2011, 10(2), 127) Aberrant regulation of JAK/STAT pathways has been implicated in multiple human pathological diseases, including cancer (JAK2) and rheumatoid arthritis (JAK1, JAK3). A gain-of-function mutation of JAK2 (JAK2V617F) has been discovered with high frequency in MPN patients. (Levine R L, et al. Cancer Cell 2005, 7, 387) The mutation in the JH2 pseudokinase domain of JAK2 leads to constitutively kinase activity. Cells containing the JAK2V617F mutation acquire cytokine-independent growth ability and often become tumor, providing strong rationale for the development of JAK inhibitors as a targeted therapy. In addition, hyperactivation of the JAK2/signal transducers and activators of transcription 3 (JAK2/STAT3) is responsible for abnormal dendritic cell differentiation leading to abnormal dendritic cell differentiation and accumulation of immunosuppressive myeloid cells in cancer (Nefedova Y, et al. Cancer Res 2005, 65, 9525). In Pten-null senescent tumors, activation of the JAK2/STAT3 pathway establishes an immunosuppressive tumor microenvironment that contributes to tumor growth and chemoresistance (Toso A, et al. Cell Reports 2014, 9, 75). JAK2 gene fusions with the TEL(ETV6) (TEL-JAK2) and PCM1 genes have been found in leukemia patients. (Lacronique V, et al. Science 1997, 278, 5341, 1309-12. Reiter A, et al. Cancer Res. 2005, 65, 7, 2662-7.) It was reported that JAK/STAT3 signaling pathway was aberrantly increased in EGFR inhibitor-resistant EGFR-mutant non-small cell lung cancer (NSCLC) cells, and JAK2 inhibition overcomes acquired resistance to EGFR inhibitors that support the use of combination therapy with JAK and EGFR inhibitors for the treatment of EGFR-dependent NSCLC. (Gao S P, et al. Sci Signal. 2016, 9 (421):ra33) JAK/STAT3 signaling promotes cancer hallmarks in the tumor and its environment, including proliferation, survival, angiogenesis, tumor metabolism while suppressing antitumor immunity. (Buchert M, et al. Oncogene, 2016, 35, 939-951) Inhibition of cytokine-dependent activation of the JAK/STAT3 pathway with JAK inhibitors may also afford orthogonal treatment opportunities for other oncogene-addicted cancer cells that have gained drug resistance. Focal amplification of JAK2 gene was observed in postchemotherapy triple-negative breast cancers (TNBCs) in a group of 9p24-amplified tumors, suggesting a role in tumorigenicity and chemoresistance. (Balko J M, et al. Sci Transl Med. 2016, 8(334):ra53)

c-Src is a nonreceptor tyrosine kinase. The Src family (SFK) comprises of eight members in humans (Src, Fyn, Yes, Lyn, Lck, Hck, Blk and Fgr) with a molecular weight between 52-62 KDa. Src and its family members are deregulated in many types of cancer. Src is a key downstream transducer of many RTKs, including EGFR, HER2, and c-Met. Activation of Src signaling has been implicated in conferring therapeutic resistance to targeted antiendocrine therapies, receptor tyrosine kinase therapies, traditional chemotherapies, and radiation therapies. (Zhang S, et al Trends Pharmacol Sci. 2012, 33, 122). SRC can promote signaling from growth factor receptors in a number of ways including participation in signaling pathways required for DNA synthesis, control of receptor turn-over, actin cytoskeleton rearrangement, migration, adhesion, invasion, motility, and survival. (Bromann P A, Oncogene 2004, 23, 7957-7968) A prominent role of Src in tumor progression-related events such as the epithelial mesenchymal transition (EMT) and the development of metastasis have been reported through the interaction with the potent metastasis suppressor, N-myc downstream regulated gene 1 (NDRG1), that regulates cancer cell migration by inhibiting Src activity. (Liu W, et al. Oncotarget. 2015, 6: 35522-35541) Although EGFR inhibitors have achieved a significant success in the majority of NSCLC patients harbor EGFR-activating mutations, a subset of patients with EGFR mutations are refractory to EGFR-TKIs. Resistance to EGFR inhibitors reportedly involves SRC activation and induction of epithelial-to-mesenchymal transition (EMT). The primary resistance to EGFR-TKIs is associated with higher levels of CRIPTO1 expression. CRIPTO1 activated SRC and ZEB1 to promote EMT via microRNA-205 (miR-205) downregulation. Recently it was reported that saracatinib, a selective SRC inhibitor, can re-sensitize ALK inhibitor-resistant cell lines, demonstrating a therapeutic role of SRC inhibition in overcoming ALK inhibitor resistance. (Crystal A S, et al. Science 2014, 346, 1480-1486)

Focal Adhesion Kinase (FAK) is a 125 kDa non-receptor tyrosine kinase and plays a significant role in adhesion, survival, motility, metastasis, angiogenesis, lymphangiogenesis, cancer stem cell functions, tumor microenvironment and epithelial to mesenchymal transition (EMT). (Golubovskaya V M, Front Biosci (Landmark Ed).; 19: 687-706) Nuclear FAK controls chemokine transcription, Tregs, and evasion of antitumor immunity, and the small-molecule FAK kinase inhibitor VS-4718 drives depletion of Tregs and promotes a CD8+ T cell-mediated anti-tumor response. (Serrels A, et al, Cells 2015, 163, 160-173). Therefore, FAK inhibitors may trigger immune-mediated tumor regression. FAK is hyperactivated in human pancreatic ductal adenocarcinoma (PDAC) and correlates with immunosuppressive tumor microenvironment (TME). Targeting focal adhesion kinase renders pancreatic cancers responsive to checkpoint immunotherapy by overcoming the fibrotic and immunosuppressive PDAC TME in mouse models. (Jiang H, et al. Nat Med. 2016, Jul. 4 [Epub ahead of print]).

It has been discovered that the compounds described herein have been surprisingly shown to be inhibitors of all three of FAK, SRC and JAK2 and can be used in combination with an EGFR inhibitor to treat cancer in a patient in need of such treatment. In some embodiments, the combination of a compound that inhibits FAK, SRC and JAK2 with an EGFR inhibitor can provide a synergistic response in a patient in need of treatment for cancer. In some embodiments, methods for treating cancer comprising administering a combination of a therapeutically effective amount of a compound that inhibits FAK, SRC and JAK2 and a therapeutically effective amount of an EGFR inhibitor. In some embodiments, the compound that inhibits FAK, SRC and JAK2 and the EGFR inhibitor are co-formulated. In some embodiments, the compound that inhibits FAK, SRC and JAK2 and the EGFR inhibitor are administered at the same time. In some embodiments, the compound that inhibits FAK, SRC and JAK2 and the EGFR inhibitor are individually formulated, and administered at the same time. In some embodiments, the compound that inhibits FAK, SRC and JAK2 and the EGFR inhibitor are individually formulated, and administered in sequence. In some embodiments, the sequential administration of the compound that inhibits FAK, SRC and JAK2 and the EGFR inhibitor can be accomplished with the compound that inhibits FAK, SRC and JAK2 administered first, and the EGFR inhibitor administered second. In some embodiments, the sequential administration of the compound that inhibits FAK, SRC and JAK2 and the EGFR inhibitor can be accomplished with EGFR inhibitor administered first, and the compound that inhibits FAK, SRC and JAK2 administered second.

In some embodiments, the compound that inhibits FAK, SRC and JAK2 is of the formula I or II

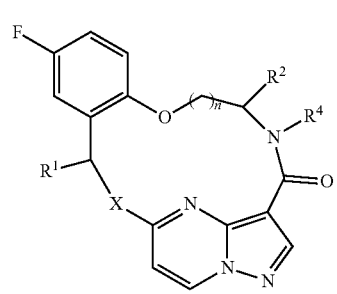

or

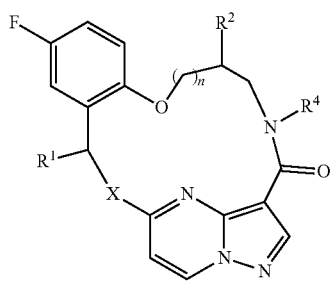

wherein

X is $NR^3$ or $CHR^3$;

each of $R^1$ and $R^2$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^5$, —$C(O)OR^5$ or —$C(O)NR^5R^6$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, —C₃-C₆ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^5$;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC₁-C₆ alkyl, —NH₂, —NH(C₁-C₆ alkyl), —N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, $C_3$-$C_6$ cycloalkyl, or monocyclic 5- to 7-membered heterocycloalkyl;

each $R^5$ and $R^6$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or heteroaryl; and n is 0 or 1;

or a pharmaceutically acceptable salt thereof.

In some embodiments, $R^1$ is H or $C_1$-$C_6$ alkyl. In some embodiments, $R^1$ is H or methyl. In some embodiments, $R^1$ is H. In some embodiments, $R^1$ is methyl. In some embodiments, $R^2$ is H. In some embodiments, $R^2$ is $C_1$-$C_6$ alkyl. In some embodiments, $R^2$ is methyl. In some embodiments, $R^2$ is —$OR^5$. In some embodiments, $R^2$ is —$OR^5$, wherein $R^5$ is H. In some embodiments, X is $NR^3$. In some embodiments, X is $CHR^3$. In some embodiments, $R^3$ is H. In some embodiments, $R^4$ is H. In some embodiments, n is 0. In some embodiments, n is 1.

Macrocyclic compounds that have been shown herein to be potent small-molecule multi-target kinase inhibitors showing activity against FAK, SRC and JAK2 include, but are not limited to, (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (also herein referred to as "Compound 1"), represented by the formula

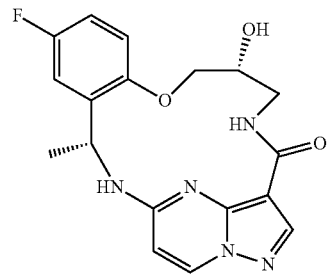 [SMILES: C[C@H]1Nc2ccn3ncc(c3n2)C(=O)NC[C@@H](O)COc2ccc(F)cc21]

(7R,14R)-12-fluoro-7-hydroxy-14-methyl-5,6,7,8,14,15-hexahydro-4H-1,16-ethenopyrazolo[4,3-g][1,5,9,11]benzoxatriazacyclotetradecin-4-one (also herein referred to as "Compound 2"), represented by the formula and 12-fluoro-5,6,7,8,14,15-hexahydro-4H-1,16-ethenopyrazolo[4,3-g][1,5,9]benzoxadiazacyclotetradecin-4-one (also herein referred to as "Compound 3"), represented by the formula

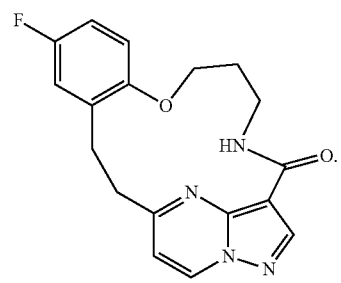 [SMILES: O=C1NCCCOc2ccc(F)cc2CCc2ccn3ncc1c3n2]

Compounds 1-3 have properties, including anti-tumor properties, which are pharmacologically mediated through inhibition of receptor and non-receptor tyrosine kinases. Compounds 1-3 are disclosed in International Patent Publication WO2015/112806, which is incorporated herein by reference for the preparation of Compounds 1, 2 and 3.

In some embodiments of the above aspects, the compound that inhibits FAK, SRC and JAK2 is of the formula

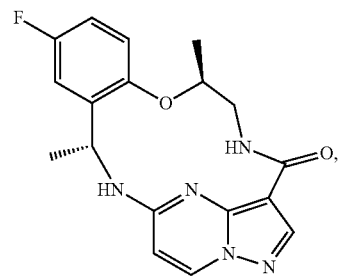 [SMILES: C[C@H]1CNC(=O)c2cnn3ccc(nc23)N[C@H](C)c2cc(F)ccc2O1]

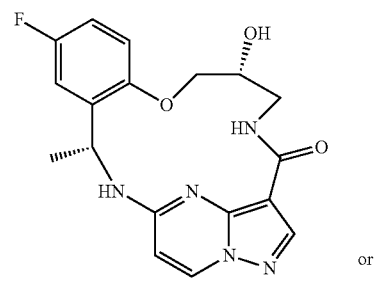

or

-continued

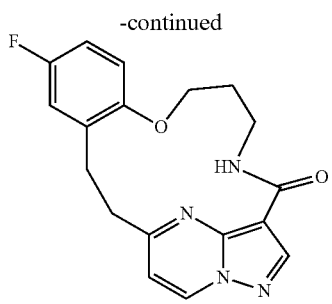

or a pharmaceutically acceptable salt thereof.

It will be appreciated that the cancer can be any cancer that may be mediated by or associated with EGFR, the upregulation of EGFR or any EGFR mutation, including but not limited to, ALCL, NSCLC, neuroblastoma, inflammatory myofibroblastic tumor, adult renal cell carcinoma, pediatric renal cell carcinoma, breast cancer, ER$^+$ breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer and lung cancer.

In some embodiments, the present disclosure provides methods of treating disease in a patient that has received a prior treatment with one or more therapeutic agents. In some embodiments, the patient has been previously treated with one or more chemotherapeutic agents. In still other embodiments, the patent has been previously treated with one or more chemotherapeutic agents and developed an acquired resistance to the treatment. In still other embodiments, the patent has been previously treated with one or more chemotherapeutic agents and developed bypass resistance to the treatment. In still other embodiments, the patent has been previously treated with one or more chemotherapeutic agents and developed bypass resistance to the treatment regulated by FAK, SRC or JAK2.

Other chemotherapeutic agents which the patient may be been treated with prior to treatment with one or more of the compounds described herein include but are not limited to kinase inhibitors, adrenocorticoids and corticosteroids, alkylating agents, peptide and peptidomimetic signal transduction inhibitors, antiandrogens, antiestrogens, androgens, aclamycin and aclamycin derivatives, estrogens, antimetabolites, platinum compounds, amanitins, plant alkaloids, mitomycins, discodermolides, microtubule inhibitors, epothilones, inflammatory and proinflammatory agents, purine analogs, pyrimidine analogs, camptothecins and dolastatins.

It will be appreciated that the EGFR inhibitor for use in connection with the combination therapy described herein can be any EGFR inhibitor as defined herein. Suitable examples of EGFR inhibitors include antibodies of EGFR or small molecule inhibitors of EGFR. In some embodiments, the EGFR inhibitor can be afatinib, brigatinib, cetuximab, canertinib (CI-1033), dacomitinib, eroltinib, gefitinib, HKI 357, icotinib, lapatinib, osimertinib, naquotinib, nazartinib, necitumumab, neratinib, olmutinib, panitumumab, PF-06747775, rociletinib, vandetanib, or pharmaceutically acceptable salts thereof. In some embodiments, the EGFR inhibitor can be cetuximab, necitumumab or panitumumab.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 m/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

EXAMPLES

Chemicals and Reagents

Compound 1, 2 and 3 were prepared according to the methods described in WO2015/112806, see specifically Examples 90, 93 and 103 as described therein. WO2015/112806 is incorporated herein by reference for the preparation of Compounds 1, 2 and 3.

Gefitinib was purchased from Tocris Bioscience. Osimertinib (AZD9291) was purchased from Selleck chemicals. Drugs were prepared in dimethyl sulfoxide (DMSO) at a concentration of 10-100 mmol/L stock solutions and stored at −20° C. Further dilutions were made in culture medium to final concentration before use. Phospho-EGFR (Tyr1068), phospho-EGFR (Tyr845), phospho-STAT3 (Tyr705), phospho-AKT (Ser473), phospho-ERK1/2 (Thr202/Tyr204), phospho-paxillin (Tyr118), phospho-YAP1 (Ser127), phospho-TRKB and β-actin antibodies were purchased from Cell Signaling Technology (Beverly, Mass.). Phospho-YAP1 (Tyr357) was purchased from Abcam (Cambridge, UK). IRDye 800CW goat anti-rabbit, and IRDye 800CW goat anti-mouse antibodies were purchased from LI-COR Biosciences.

Cell Lines

Human lung adenocarcinoma PC-9 cells, harboring EGFR exon 19 deletion (E746-A750) were provided by F. Hoffmann-La Roche Ltd. with the authorization of Dr. Mayumi Ono (Kyushu University, Fukuoka, Japan). Human lung adenocarcinoma H1975 cells, harboring both sensitizing L858R and resistant T790M mutation, were purchased from the American Type Culture Collection (ATCC). All cell lines were maintained in RPMI (Roswell Park Memorial Institute medium) 1640 supplemented with 1% penicillin/streptomycin/glutamine (Gibco) and 10% fetal bovine serum (FBS) (Gibco) in 5% $CO_2$, 37° C. cell culture incubator and were routinely evaluated for mycoplasma contamination.

In-Vitro Assays

Example 1: Cell Viability Assay

Cells were seeded on 96-well plates at the following densities: $2 \times 10^3$, $3 \times 10^3$ and $4 \times 10^3$ and incubated for 24 hours. Next, the cells were treated with serial dilutions of the drugs administered at doses typically corresponding to ⅛, ¼, ½, ⅝, ¾, ⅞, 1, 1.5 and 2 of the individual IC50 values. After 72 hours of incubation, 0.5 mg/ml of MTT (tetrazolium-based semiautomated colorimetric 3(4,5-dimethylthiazol-2-yl)-2,5-diphenyltetrazolium bromide) reagent (Sigma Aldrich) was added to the medium in the wells for 2 hours at 37° C., formazan crystals in viable cells were solubilized with 100 μl DMSO and spectrophotometrically quantified using a microplate reader (Varioskan Flash Thermo Electron) at 550 nm of absorbance. Fractional survival was then calculated by dividing the number of cells in drug-treated wells by the number of cells in control wells. Data of combined drug effects were subsequently analyzed by the Chou and Talalay method (See Chou T C. Drug combination studies and their synergy quantification using the Chou-Talalay method. Cancer research. 2010; 70:440-6). Combination Index (CI) values <1, =1 and >1 indicated synergism, additive effect and antagonism, respectively.

Figure 1B:
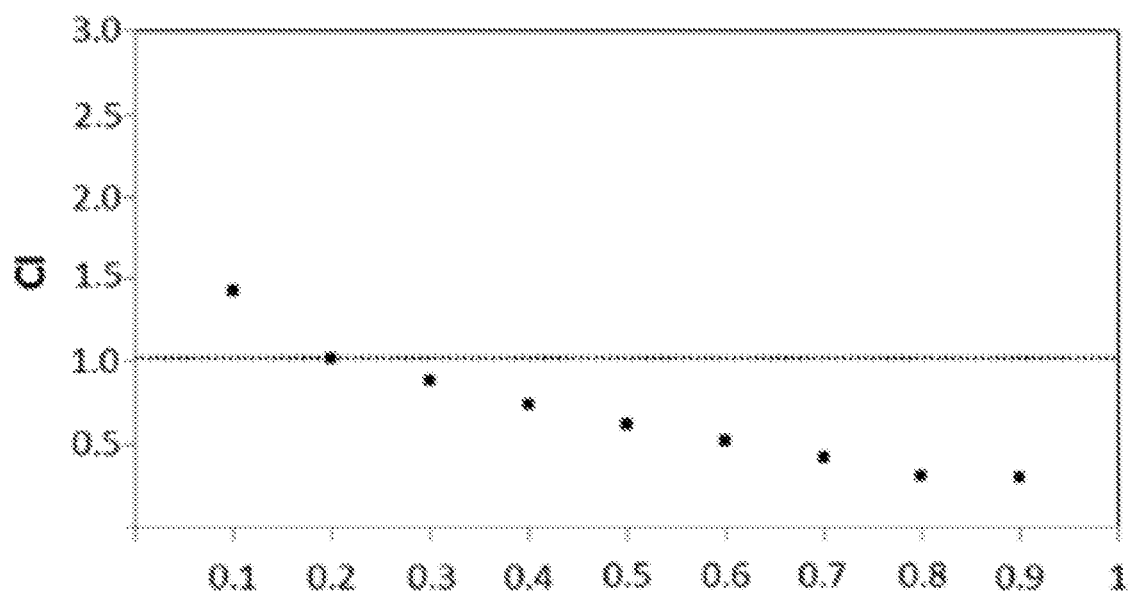
FIG. 1b shows the Combination Index (CI) of the EGFR inhibitor gefitinib and Compound 1 in PC9 cells. CI=0.685.
Figure 2A:
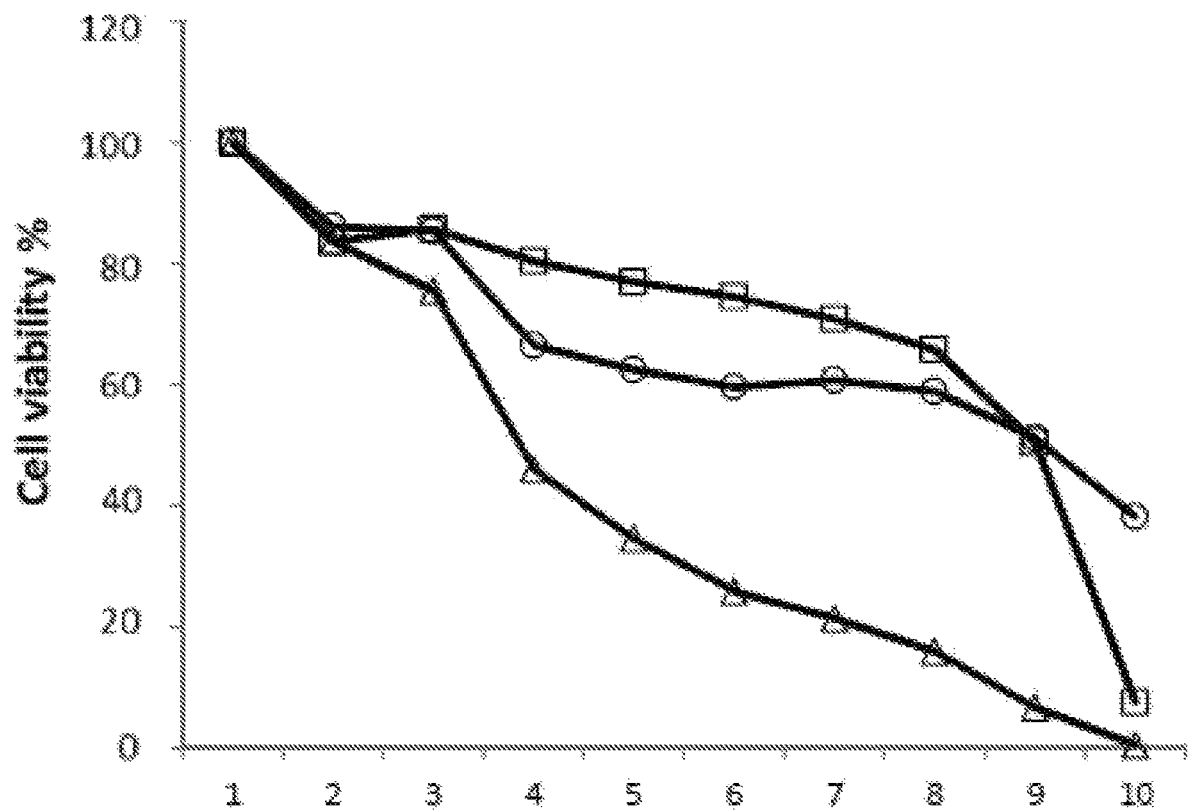
FIG. 2a shows cell viability % of the EGFR inhibitor osimertinib, Compound 1, and osimertinib and Compound 1 in PC9 cells at various doses. (○) osimertinib; (□) Compound 1; (Δ) osimertinib+Compound 1.
Figure 2B:
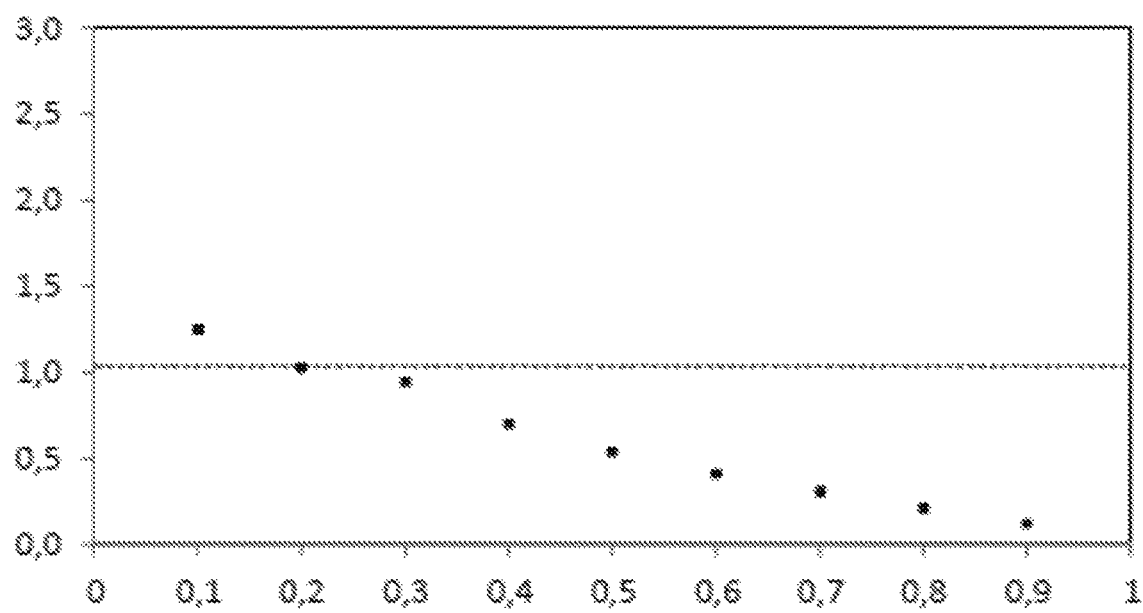
FIG. 2b shows the Combination Index (CI) of the EGFR inhibitor osimertinib and Compound 1 in PC9 cells. CI=0.600.

Results showing cell viability % of the EGFR inhibitor (gefitinib or osimertinib), Compound 1, and the of the EGFR inhibitors with Compound 1 in PC9 cells are shown in FIGS. 1a and 2a. Results showing the corresponding Combination Index (CI) are shown in FIGS. 1b and 2b.

Figure 3A:
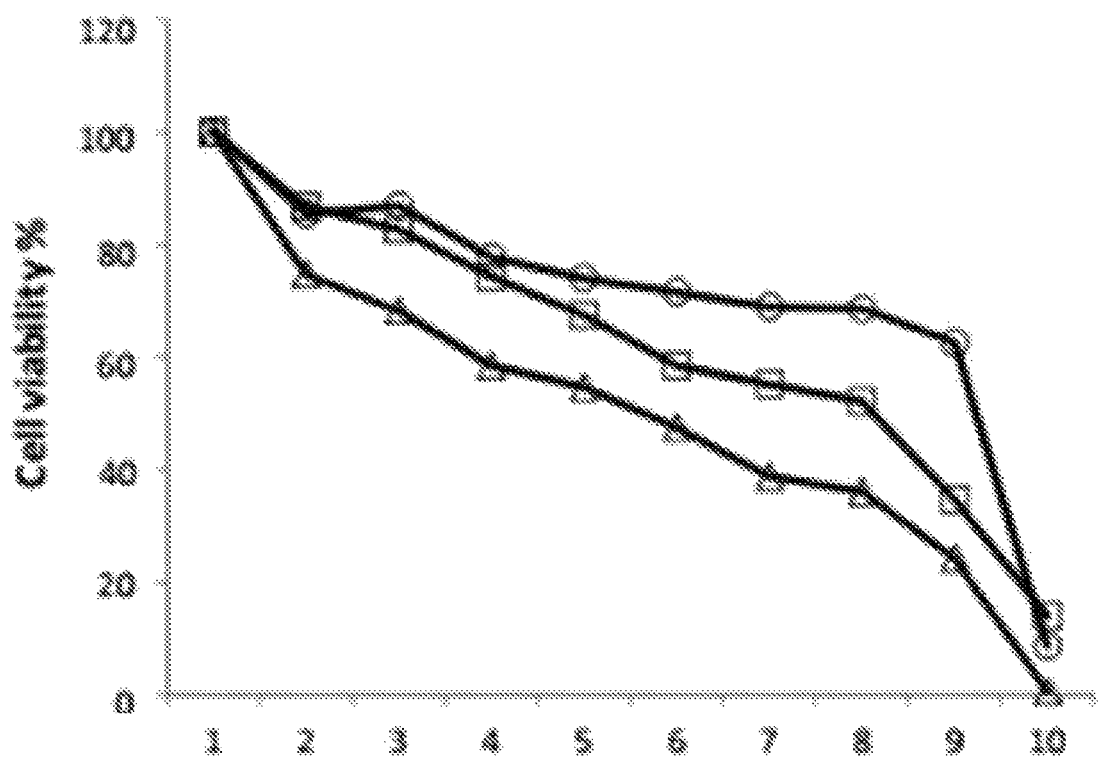
FIG. 3a shows cell viability % of the EGFR inhibitor gefitinib, Compound 1, and gefitinib and Compound 1 in H1975 cells at various doses. (○) gefitinib; (□) Compound 1; (Δ) gefitinib+Compound 1.
Figure 3B:
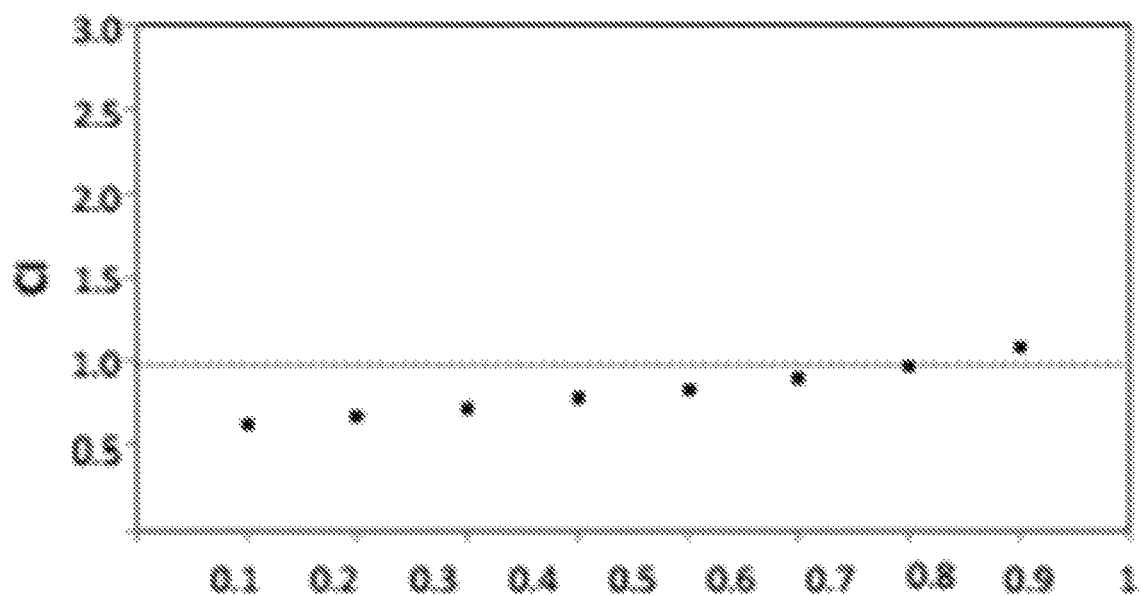
FIG. 3b shows the Combination Index (CI) of the EGFR inhibitor gefitinib with Compound 1 in H1975 cells. CI=0.845.
Figure 4A:
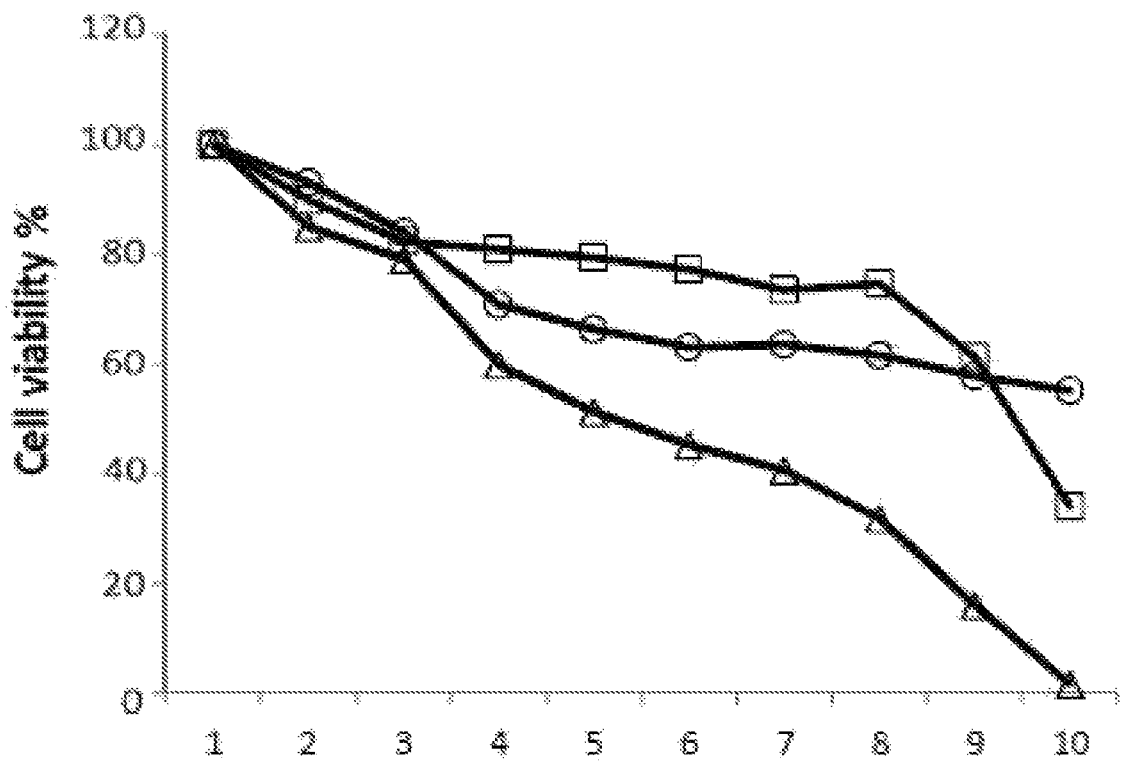
FIG. 4a shows cell viability % of the EGFR inhibitor osimertinib, Compound 1, and osimertinib and Compound 1 in H1975 cells at various doses. (○) osimertinib; (□) Compound 1; (Δ) osimertinib+Compound 1.
Figure 4B:
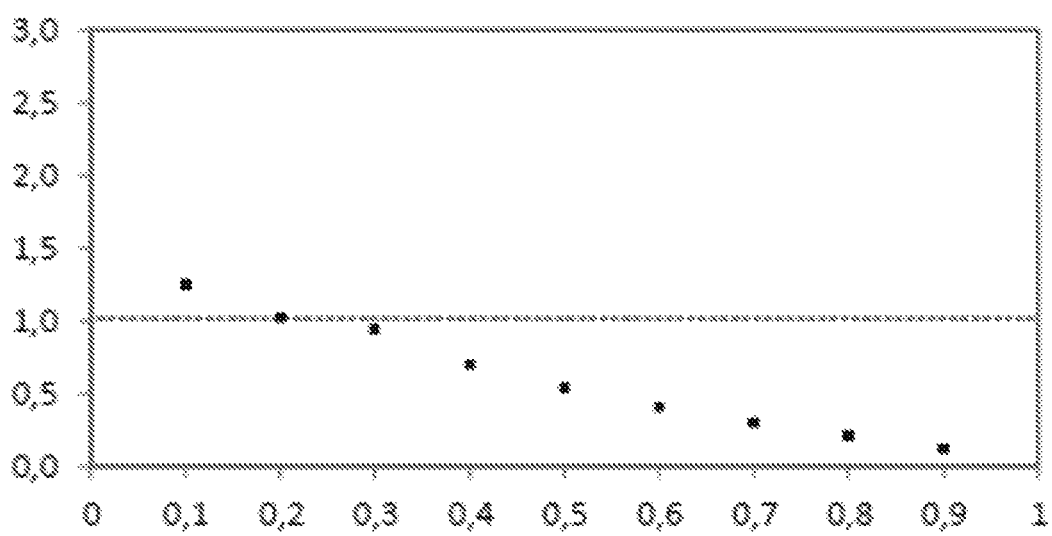
FIG. 4b shows the Combination Index (CI) of the EGFR inhibitor osimertinib with Compound 1 in H1975 cells. CI=0.612.

Results showing cell viability % of the EGFR inhibitor (gefitinib or osimertinib), Compound 1, and the combination of the EGFR inhibitors with Compound 1 in H1975 cells are shown in FIGS. 3a and 4a. Results showing the corresponding Combination Index (CI) are shown in FIGS. 3b and 4b.

Example 2: Colony Formation Assay

Cells were plated in six-well plates at 1000 cells/well in RPMI, 10% FBS. The cells were cultured for 24 hours and the media were then replaced with RPMI, 1% FBS with or without inhibitors. After 72 hours the media were removed and replaced with fresh media without inhibitors for a total of 10 days. At the end of the experiment, the media were removed and the cells were washed with phosphate-buffered saline (PBS). The colonies were fixed and stained simultaneously with 0.5% crystal violet in 10% of ethanol for 15 min. The stain was aspirated and the wells were washed with deionized water until the background was clear. The wells were then photographed. As a semiquantitative measurement, the crystal violet was extracted from the colonies with Triton X-100 0.5% solution overnight and the absorbance was measured at 570 nm.

Figure 5A:
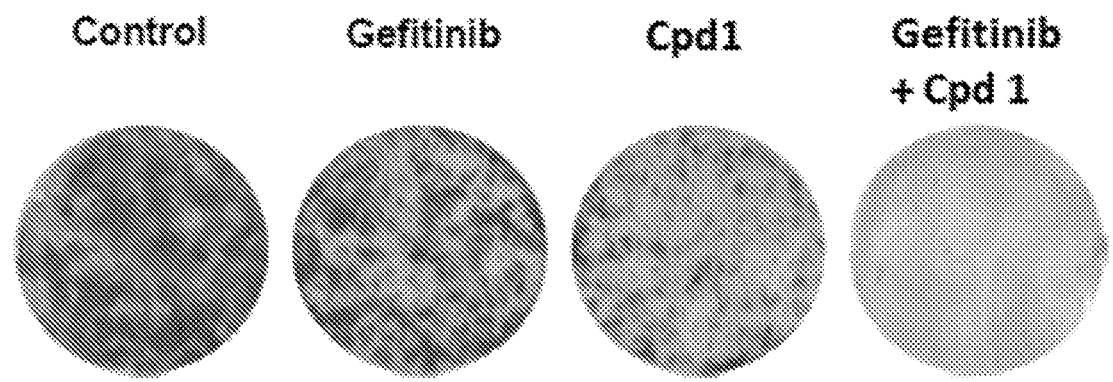
FIG. 5a shows colonization images of control, EGFR inhibitor gefitinib, Compound 1, and the combination of gefitinib with Compound 1 in PC9 cells.
Figure 5B:
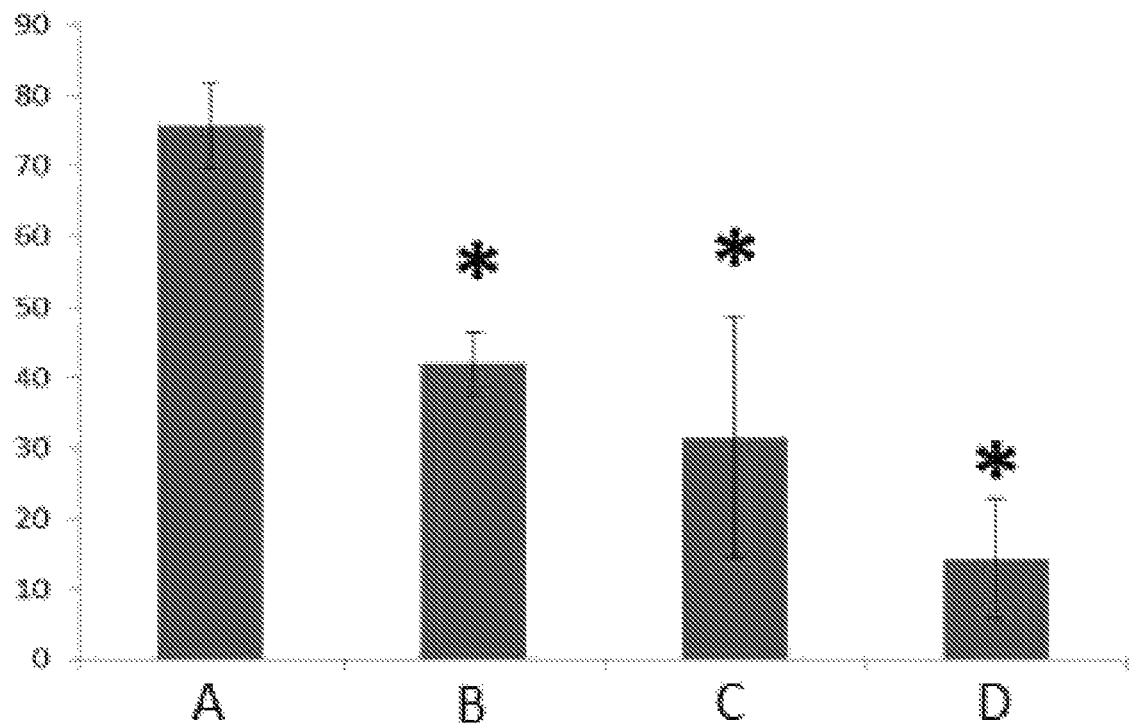
FIG. 5b shows the graphical representation of the % area colonized of control, EGFR inhibitor gefitinib, Compound 1, and the combination of gefitinib with Compound 1 in PC9 cells. (A) Control; (B) gefitinib; (C) Compound 1; (D) gefitinib+Compound 1.
Figure 6A:
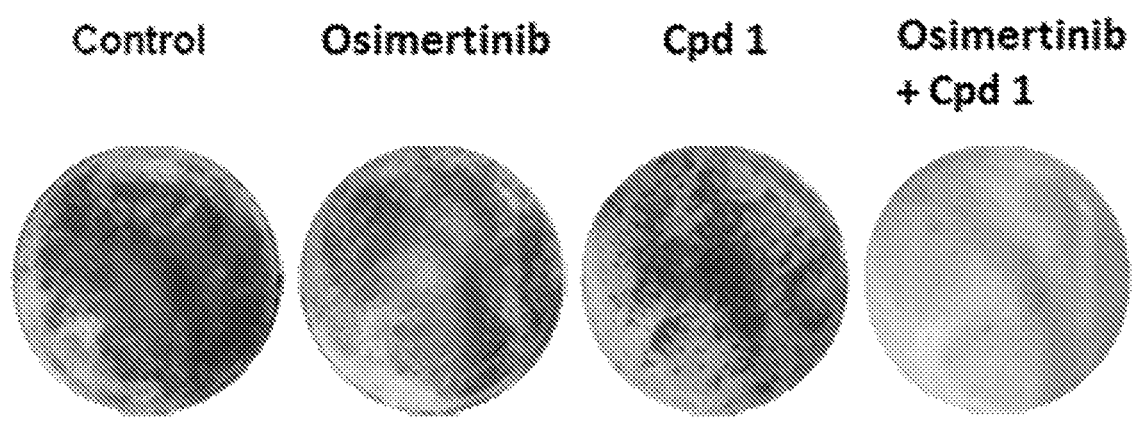
FIG. 6a shows colonization images of control, EGFR inhibitor osimertinib, Compound 1, and the combination of osimertinib with Compound 1 in PC9 cells.
Figure 6B:
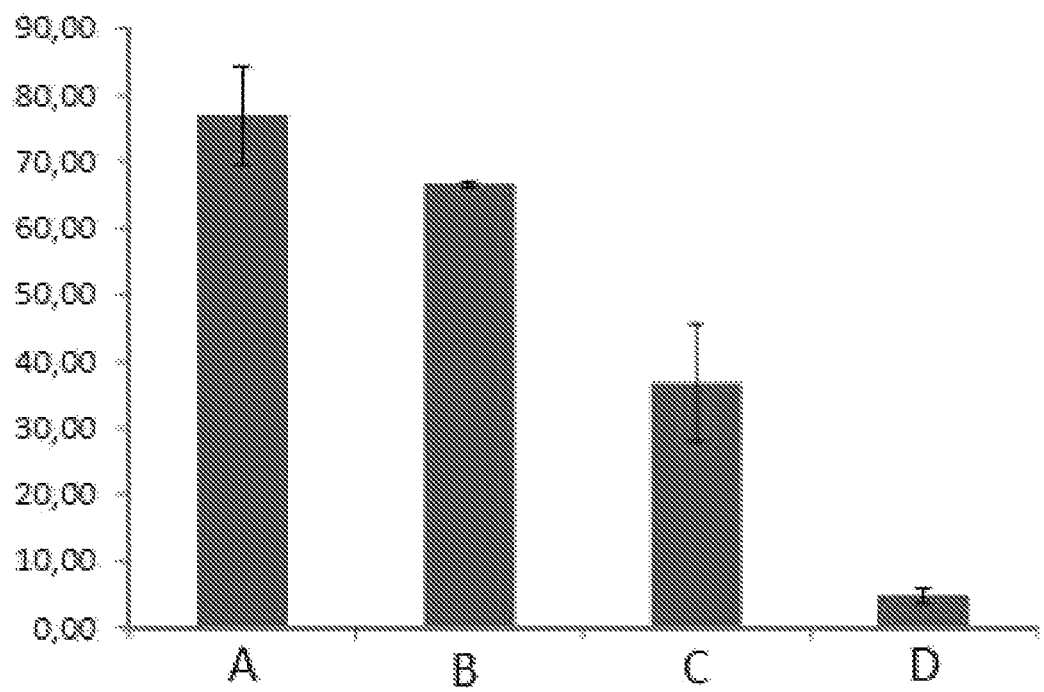
FIG. 6b shows the graphical representation of the % area colonized of control, EGFR inhibitor osimertinib, Compound 1, and the combination of osimertinib with Compound 1 in PC9 cells. (A) Control; (B) osimertinib; (C) Compound 1; (D) osimertinib+Compound 1.

Results showing colonization images of the control, the EGFR inhibitor (gefitinib or osimertinib), Compound 1, and the combination of the EGFR inhibitors with Compound 1 in PC9 cells are shown in FIGS. 5a and 6a. Results showing the graphical representation of the % area colonized are shown in FIGS. 5b and 6b.

Figure 7A:
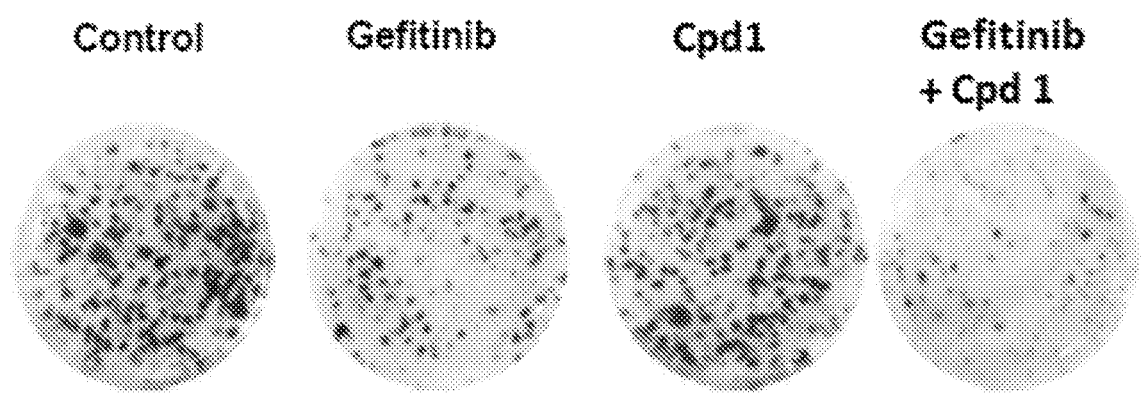
FIG. 7a shows colonization images of control, EGFR inhibitor gefitinib, Compound 1, and the combination of gefitinib with Compound 1 in H1975 cells.
Figure 7B:
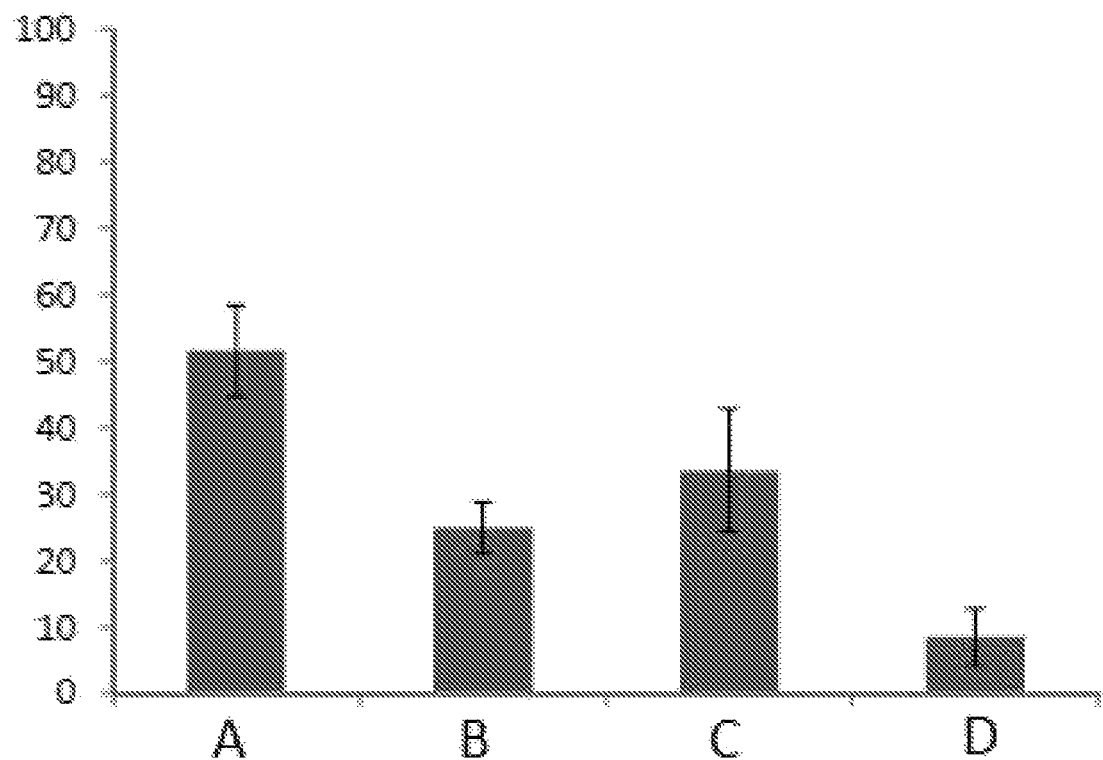
FIG. 7b shows the graphical representation of the % area colonized of control, EGFR inhibitor gefitinib, Compound 1, and the combination of gefitinib with Compound 1 in H1975 cells. (A) Control; (B) gefitinib; (C) Compound 1; (D) gefitinib+Compound 1.
Figure 8A:
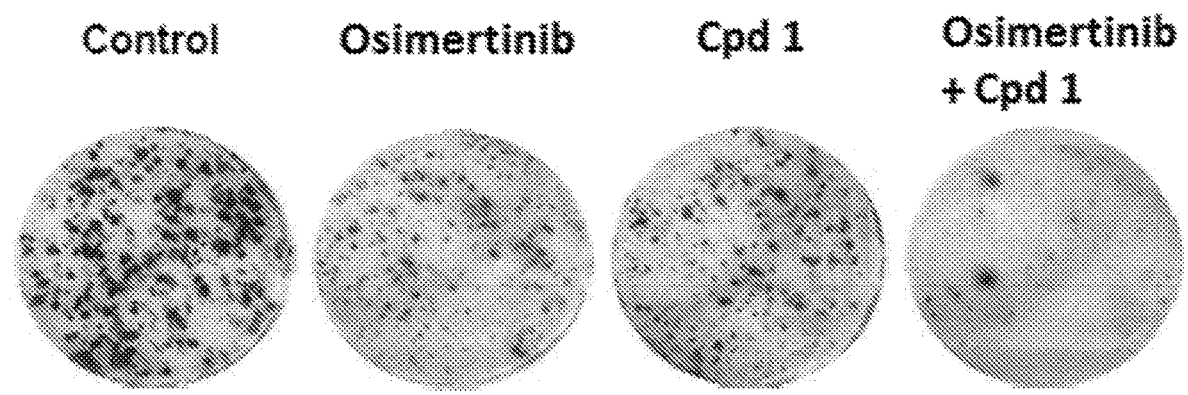
FIG. 8a shows colonization images of control, EGFR inhibitor osimertinib, Compound 1, and the combination of osimertinib with Compound 1 in H1975 cells.
Figure 8B:
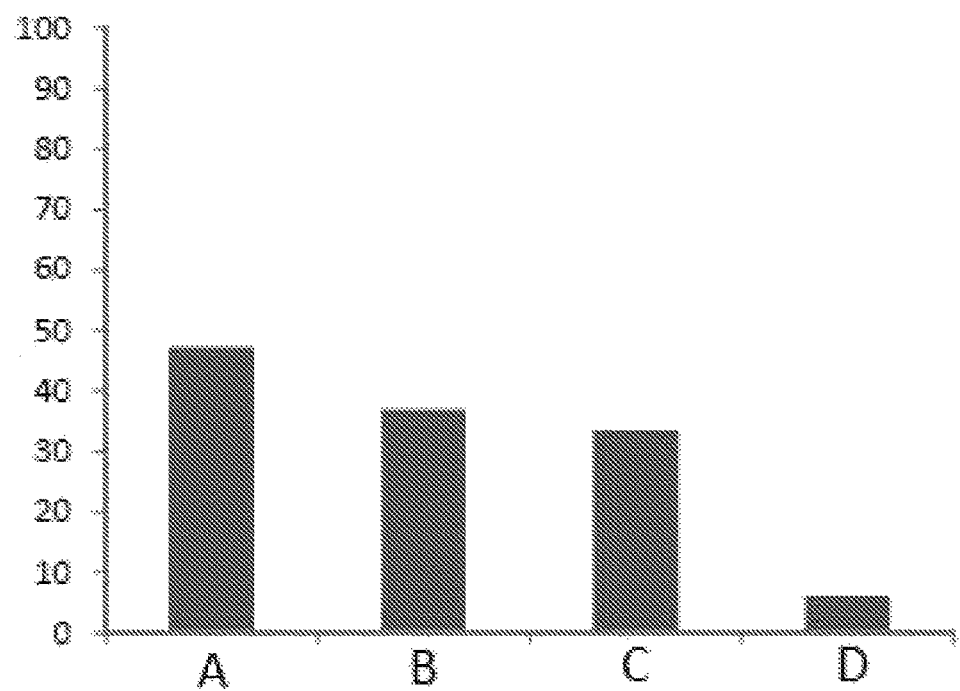
FIG. 8b shows the graphical representation of the % area colonized of control, EGFR inhibitor osimertinib, Compound 1, and the combination of osimertinib with Compound 1 in H1975 cells. (A) Control; (B) osimertinib; (C) Compound 1; (D) osimertinib+Compound 1.

Results showing colonization images of the control, the EGFR inhibitor (gefitinib or osimertinib), Compound 1, and the combination of the EGFR inhibitors with Compound 1 in H1975 cells are shown in FIGS. 7a and 8a. Results showing the graphical representation of the % area colonized are shown in FIGS. 7b and 8b.

Example 3. Enzymatic Kinase Inhibition Assay 1

The enzymatic kinase inhibition against FAK, SRC and JAK2 were evaluated at Eurofins using the Erofins KinaseProfiler™ panel. All compounds were prepared to a working stock of 50× final assay concentration in 100% DMSO. Where appropriate, more concentrated stocks were diluted manually to 50× using 100% DMSO. Compounds supplied as powders were reconstituted to a 10 mM stock in 100% DMSO before further dilution to 50×. The required volume of the 50× stock of test compound was added to the assay well, before a reaction mix containing the enzyme and substrate was added. The reaction was initiated by the addition of ATP at 10 µM concentration. There was no pre-incubation of the compound with the enzyme/substrate mix prior to ATP addition. Data are handled using a custom built in-house analysis software. Results are expressed as kinase activity remaining, as a percentage of the DMSO control. This is calculated using the following formula: (Mean of Sample Counts Mean of Blank Counts)/Mean of Control Counts.

TABLE 1

| Compound # | % remaining FAK at 1 µM testing comp. | % remaining SRC at 1 µM testing comp. | % remaining JAK2 at 1 µM testing comp. |
|---|---|---|---|
| 1 | −1 | 1 | 0 |
| 2 | −1 | 2 | 3 |
| 3 | −2 | 8 | 6 |

Example 4. Enzymatic Kinase Inhibition Assay 2

The kinase inhibition $IC_{50}$ was determined at Reaction Biology Corporation (www.reactionbiology.com, Malvern, Pa.) following the procedures described in the reference (Anastassiadis T, et al Nat Biotechnol. 2011, 29, 1039). Specific kinase/substrate pairs along with required cofactors were prepared in reaction buffer; 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2). Compounds were delivered into the reaction, followed ~20 minutes later by addition of a mixture of ATP (Sigma, St. Louis Mo.) and $^{33}P$ ATP (Perkin Elmer, Waltham Mass.) to a final concentration of 10 µM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. $IC_{50}$ values and curve fits were obtained using Prism (GraphPad Software).

TABLE 2

| Compound # | FAK $IC_{50}$ (nM) | SRC $IC_{50}$ (nM) | JAK2 $IC_{50}$ (nM) |
|---|---|---|---|
| 1 | 6.96 | 5.29 | 1.04 |

Example 5. NCI-H1975 Lung Cancer Cell Proliferation Assay

Figure 9:
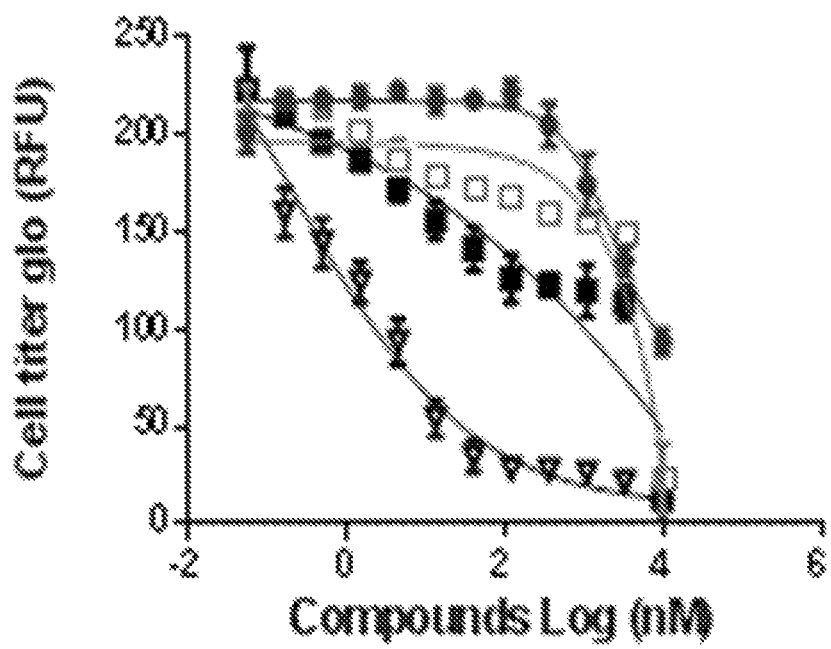
FIG. 9 shows anti-proliferation of Compound 1, osimertinib, or the combination of Compound 1 and osimertinib in NCI-H1975 Cells. (●) Compound 1, $IC_{50}$=4000 nM; (□) osimertinib, $IC_{50}$ (partial)=13.4 nM; (■) Compound 1 (1 μM)+osimertinib, $IC_{50}$=100 nM; (V) Compound 1 (3 μM)+osimertinib, $IC_{50}$=3 nM.
Figure 10:
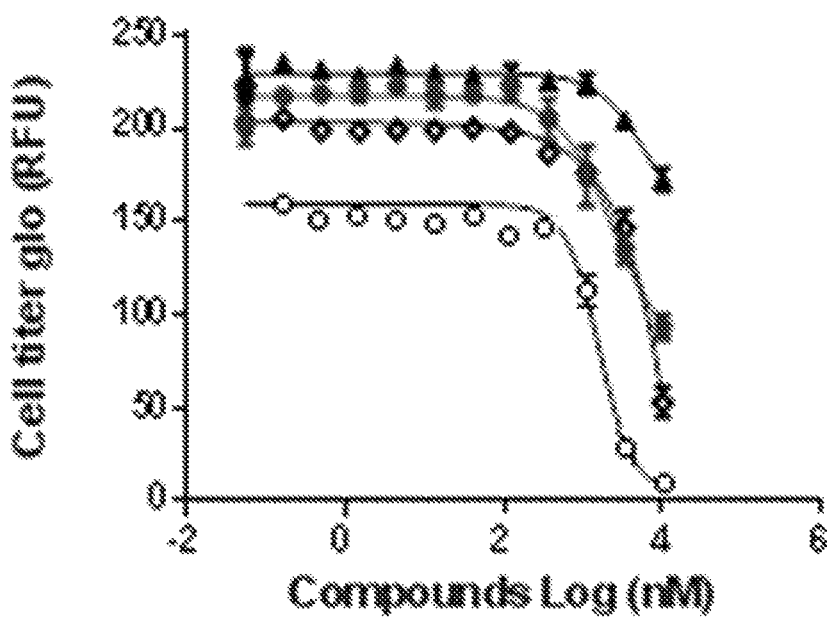
FIG. 10 shows anti-proliferation of Compound 1, erlotinib, or the combination of Compound 1 and erlotinib in NCI-H1975 Cells. (●) Compound 1, $IC_{50}$=4000 nM; (Δ) erlotinib, $IC_{50}$=6236 nM; (♦) Compound 1 (1 μM)+erlotinib, $IC_{50}$=5000 nM; (○) Compound 1 (3 μM)+erlotinib $IC_{50}$=1000 nM.

Five thousand NCI-H1975 cells per well were seeded in 384 well white plate for 24 hrs, and then treated with Compound 1, AZD9291(osimertinib) or erlotinib, Compound 1 at 1 mM or 3 mM plus AZD9291 or erlotinib in various concentrations for 72 hours (37° C., 5% $CO_2$). Cell proliferation was measured using CellTiter-Glo luciferase-based ATP detection assay (Promega) following the manufactures's protocol. $IC_{50}$ determinations were performed using GraphPad Prism software (GraphPad, Inc., San Diego, Calif.). The results were summarized in FIG. 9 and FIG. 10. Although NCI-H1975 lung cancer cell line endogenously expresses EGFR L858R/T790M double mutations, the third generation irreversible EGFR inhibitor AZD9291 demonstrated very partial inhibition of the cell proliferation. We investigated the synergistic effect of Compound 1 in combination with erlotinib or AZD9291 on NCI-H1975 cell proliferation. Compound 1 alone had only partial inhibition activity to NCI-H1975 at high concentration ($IC_{50}$ 4 µM). A strong synergy was observed with the combination of AZD9291 and Compound 1 AZD9291 potently inhibited NCI-H1975 with an $IC_{50}$ of 3 nM in the presence of Compound 1 at 3 µM concentration (FIG. 9). The combination caused much complete cell proliferation suppression compared to AZD9291 treatment alone. Because of the presence of T790M mutation in NCI-H1975 cell line, erlotinib is not sensitive to the inhibition of NCI-H1975 cell proliferation, and the $IC_{50}$ was improved from 6236 nM to 1000 nM when Compound 1 was present at 3 µM concentration (FIG. 10).

Example 6. Immunoblotting for Cellular Kinase Phosphorylation Assays

Figure 11:
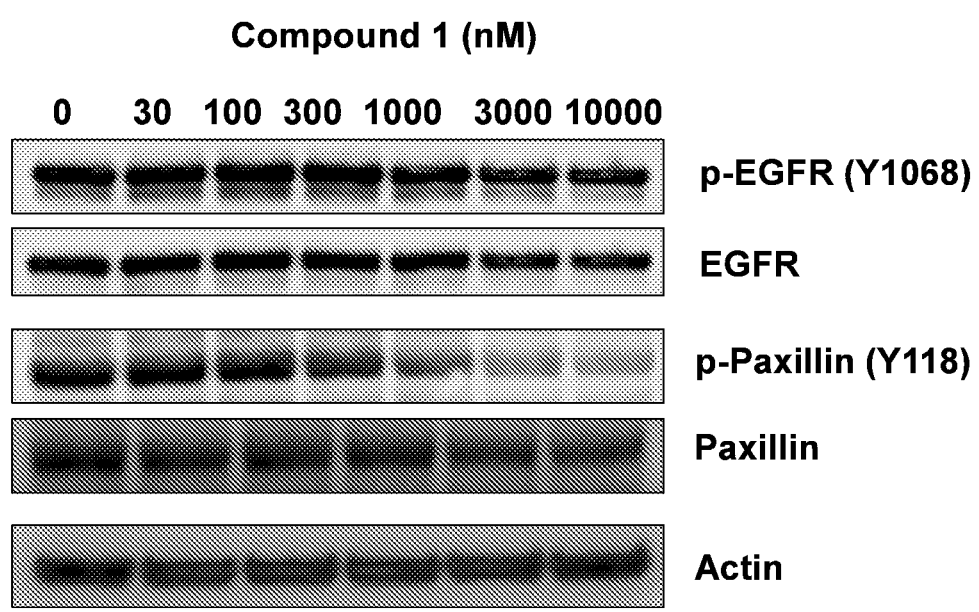
FIG. 11 shows gel images that demonstrate that Compound 1 dose-dependently inhibited the phosphorylation of paxillin.
Figure 12:
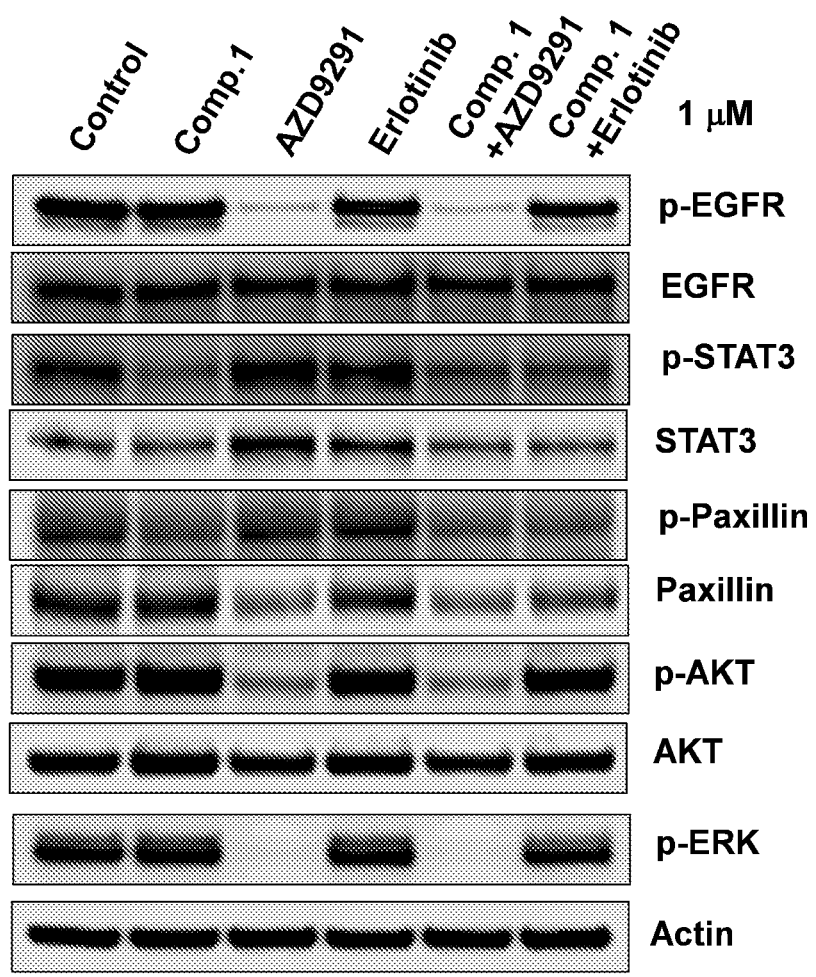
FIG. 12 shows the inhibition of STAT3, ERK and AKT signaling pathways by Compound 1, osimertinib (AZD9291), erlotinib, Compound 1+osimertinib (AZD9291), and Compound 1+erlotinib at 1 µM concentration.

NSCLC NCI-H1975 cells (harboring EGFR L858R/T790M double mutations) were cultured in RPMI medium, supplemented with 10% fetal bovine serum and 100 U/mL of penicillin/streptomycin. Half a million cells per well were seeded in 24 well plate for 24 hrs, and then treated with Compound 1, erlotinib or AZD9291, or the combination of Compound 1 with erlotinib or AZD9291 for 4 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 μg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated EGFR and total EGFR (Sigma), phosphorylated paxillin and total paxillin (Cell Signaling Technology), phosphorylated STAT3 and total STAT3 (Cell Signaling Technology), phosphorylated AKT and total AKT (Cell Signaling Technology), phosphorylated ERK (Cell Signaling Technology) and Tubulin (Sigma). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The results were summarized in FIG. 11 and FIG. 12. Compound 1 had no inhibition against EGFR phosphorylation and dose-dependently inhibited the phosphorylation of SRC/FAK substrate paxillin in NCI-H1975 cells (FIG. 11). At 1 μM concentration, Compound 1 had minimum inhibition against the phosphorylation of EGFR, AKT and ERK, and significant inhibition against the phosphorylation of STAT3 and paxillin. At 1 μM concentration, AZD9291 had significant inhibition against the phosphorylation of EGFR, AKT and ERK, and minimum inhibition against the phosphorylation of STAT3 and paxillin. At 1 μM concentration, erlotinib had minimum inhibition against the phosphorylation of EGFR, AKT, ERK, STAT3 and paxillin. The combination of Compound 1 and AZD9291 significantly inhibited the phosphorylation of EGFR, AKT, ERK, STAT3 and paxillin leading to the synergy in the antiproliferation of NCI-H1975 cells.

What is claimed is:

1. A method for treating cancer in a patient in need thereof, the method comprising the step of administering to the patient a therapeutically effective amount of a compound having structure:

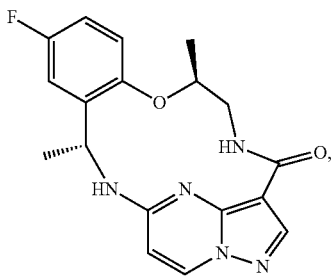

or a pharmaceutically acceptable salt thereof, and a therapeutically effective amount of an EGFR inhibitor selected from afatinib, dacomitinib, gefitinib, and osimertinib, or a pharmaceutically acceptable salt thereof, wherein the cancer is lung cancer.

2. The method of claim 1, wherein the lung cancer is non-small cell lung cancer (NSCLC), adenocarcinoma, lung squamous cell carcinoma, large cell carcinoma, large cell neuroendocrine tumor, or small cell lung cancer (SCLC).

3. The method of claim 1, wherein the lung cancer is non-small cell lung cancer or metastatic non-small cell lung cancer.

4. The method of claim 1, wherein the EGFR inhibitor is afatinib or a pharmaceutically acceptable salt thereof.

5. The method of claim 1, wherein the EGFR inhibitor is dacomitinib or a pharmaceutically acceptable salt thereof.

6. The method of claim 1, wherein the EGFR inhibitor is gefitinib, or a pharmaceutically acceptable salt thereof.

7. The method of claim 1, wherein the EGFR inhibitor is osimertinib or a pharmaceutically acceptable salt thereof.

8. The method of claim 1, comprising oral administration.

9. The method of claim 1, comprising from 0.1 mg to 1 g daily of the compound, or a pharmaceutically acceptable salt thereof.

10. The method of claim 1, comprising from 50 mg to 250 mg daily of the compound, or a pharmaceutically acceptable salt thereof.

11. The method of claim 1, comprising from 50 mg to 250 mg daily of the EGFR inhibitor, or a pharmaceutically acceptable salt thereof.

12. The method of claim 1, wherein the compound and the EGFR inhibitor are individually formulated, and administered at the same time.

13. The method of claim 1, comprising sequential administration of the compound and the EGFR inhibitor.

14. The method of claim 13, comprising administering the compound first, and administering the EGFR inhibitor second.

15. The method of claim 13, comprising administering the EGFR inhibitor first, and administering the compound second.

* * * * *